US009888690B2

(12) United States Patent
Joshi et al.

(10) Patent No.: US 9,888,690 B2
(45) Date of Patent: Feb. 13, 2018

(54) **INSECTICIDAL COMPOUNDS FROM *NOTHAPODITES FOETIDA* AND PROCESS FOR THE EXTRACTION THEREOF**

(75) Inventors: Swati Pramod Joshi, Pune (IN); John Pereira, Mysore (IN); Phool Kumar Patanjali, Gurgaon (IN); Sunita Sharad Kunte, Pune (IN); Kiran Babasaheb Sonawane, Pune (IN); Suresh Gurappa Mummigatti, Mysore (IN); Sumithra Devi Sanna, Mysore (IN); Krishnaiah Eraiah Hullukere, Mysore (IN); Seema Chaudhary, Gurgaon (IN)

(73) Assignee: COUNCIL OF SCIENTIFIC & INDUSTRIAL RESEARCH, New Delhi (IN)

(*) Notice: Subject to any disclaimer, the term of this patent is extended or adjusted under 35 U.S.C. 154(b) by 190 days.

(21) Appl. No.: 14/128,439

(22) PCT Filed: Jun. 21, 2012

(86) PCT No.: PCT/IB2012/053135
§ 371 (c)(1),
(2), (4) Date: Jun. 20, 2014

(87) PCT Pub. No.: WO2012/176145
PCT Pub. Date: Dec. 27, 2012

(65) Prior Publication Data
US 2014/0309182 A1    Oct. 16, 2014

(30) Foreign Application Priority Data
Jun. 22, 2011  (IN) .......................... 3072/DEL/2010

(51) Int. Cl.
| *A01N 43/90* | (2006.01) |
|---|---|
| *A01N 65/00* | (2009.01) |
| *A01N 65/08* | (2009.01) |
| *C07D 471/14* | (2006.01) |
| *C07H 15/26* | (2006.01) |
| *C07C 69/80* | (2006.01) |
| *A01N 37/10* | (2006.01) |

(52) U.S. Cl.
CPC ............. *A01N 43/90* (2013.01); *A01N 37/10* (2013.01); *A01N 65/00* (2013.01); *A01N 65/08* (2013.01); *C07C 69/80* (2013.01); *C07D 471/14* (2013.01); *C07H 15/26* (2013.01)

(58) Field of Classification Search
None
See application file for complete search history.

(56) References Cited
U.S. PATENT DOCUMENTS
2010/0273823 A1   10/2010  Ma et al.

FOREIGN PATENT DOCUMENTS
| WO | 1992/07856 | 5/1992 |
|---|---|---|
| WO | 1997/43290 | 11/1997 |
| WO | WO97/43290 | * 11/1997 |

OTHER PUBLICATIONS

Wahidulla et al., Phytochemistry, 1998, 48(7), pp. 1203-1206.*
Wahidulla, Solimabi et al., (1998), "Lipid constituents of the red alga *Acanthophora spicifera*", Phytochemistry, 48(7):1203-1206.
Pirillo, Angela et al., (1995), "Constituents of Nothapodytes foetida", Journal of the Chemical Society, Perkin Transactions 1: Organic and Bio-Organic Chemistry, 5:583-587.
(Continued)

Primary Examiner — Traviss C McIntosh, III
(74) Attorney, Agent, or Firm — Blank Rome LLP; Michael C. Greenbaum

(57) ABSTRACT

The present invention relates to an insecticidal enriched extract (biopesticide) isolated from the stem of *Nothapodites foetida* (Wight) Sleumer (formerly *Mappia foetida* (Miers) useful for the insect free storage and transport of grains and seed. The insecticidal activity of the enriched extract (biopesticide) of the invention is ascribed to compound/s other than camptothecin. The invention further relates to the process for preparation thereof, containing Compounds of general formula 1 and formula 2 (General formula 1) wherein $R1=CH_3$, $CH_2OAC$ and wherein $R2=COOH$, or (I) and $R3=H$. OH. (Formula 2)

12 Claims, 12 Drawing Sheets

(56) References Cited

OTHER PUBLICATIONS

Tangirala, Raghuram et al., (2006), "Synthesis and biological assays of E-ring analogs of camptothecin and homocamptothecin", Bioorganic & Medicinal Chemistry, 14(18):6202-6212.
Week 201006 Thomson Scientific. London. GB; AN 2010-A38898 XP002683787. & IN 187 517 A1 (Council Sci&Ind Res India) May 11, 2002 (May 11, 2002).

* cited by examiner

INSECTICIDAL COMPOUNDS FROM *NOTHAPODITES FOETIDA* AND PROCESS FOR THE EXTRACTION THEREOF

FIELD OF THE INVENTION

The present invention relates to an insecticidal compound of general formula 1 and formula 2 isolated from the stem of *Nothapodites foetida* (Wight.) Sleumer (formerly *Mappia foetida* (Miers)) useful for the insect free storage and transport of grains and seed. Particularly, present invention further relates to insecticidal enriched extract (biopesticide) isolated from the stem of *Nothapodites foetida* (Wight.) Sleumer (formerly *Mappia foetida*. More particularly, the insecticidal activity of the enriched extract (biopesticide) of the invention is ascribed to compound/s other than camptothecin. The present invention further relates to the process for the extraction thereof.

BACKGROUND OF THE INVENTION

Even though every plant species has an inbuilt unique chemical complex structure that protects it from/provides resistance against pests/insects; there remains a need for external pesticides that will protect the plant against those pests which are resistant to inbuilt resistance of plant.

Currently, synthetic insecticides are used to protect stored grain/seed from insect infestation. Synthetic insecticides are manufactured at least in part using synthetic chemicals created from other chemicals. Synthetic insecticides are undesirable because of ecological and toxic effects of the chemicals. They are not permitted for use on organically produced grain/seed. The continued use of synthetic insecticides has led to a large number of insect pests developing resistance to the insecticides. As a result, these insecticides have to be withdrawn or larger quantities need to be used, exacerbating the problem. The problem of insect resistance is also indicated with *Bacillus thuringiensis*, the most widely used and intensively studied microbial insecticide.

Biopesticide offer an answer to the above problems, as they are eco-friendly, non-persistent, safer to use and the chances of insect pests developing resistance is unlikely as the insecticidal activity is normally due to multi-component active ingredients.

Thus, alternative to synthetic pesticides are pesticides derived from natural materials such as animals, plants, bacteria, and certain minerals.

Preferable, biopesticides are natural plant products that belong to the so called secondary metabolites that include thousands of alkaloids, terpenoids, phenolics and minor secondary metabolites. Biopesticides have usually no known function in photosynthesis, growth or other basic aspects of plant physiology; however, their biological activity against insect pests, nematodes, fungi and other organisms is well documented.

Reference may be made to the use of plants and minerals as traditional protectants of stored products, wherein the traditional method of mixing sand with stored grain is documented. However, since the sand particles are used to block the inter granular spaces and act as a physical barrier to the movement of insect pests, large quantities of sand have to be used which is unhygienic and also necessitates sieving off the sand before using the grain. [Golob, P and Webley, D. J., (1980) G138, Chatham, UK, Natural Resources Institute]

The use of diatomaceous earth based formulations for the protection of stored grain in the USA and Australia is documented. However, the drawbacks are that the treatment inhibits the free flow of grain and also damages grain handling equipment. More recently, health problems to workers have restricted its use considerably. [Frank H. A., Grain protectants: Current status and prospects for the future, J. Stored Prod. Res. 32(4)293-302 1996]

Use of mineral dusts for protection against insect pests with special reference to cereal grains, in Grain Sanitation wherein activated clay is used as a nontoxic grain protectant is documented. [Eds. S. K. Majumder & J. S. Venugopal, Academy of Pest Control Sciences, Mysore, India, 1969, pp. 81-96]. Diatomaceous dusts have also been used as grain protectants. However, the treatment is not effective on grain with high moisture content or in regions with high relative humidity as in coastal areas as reported by Mevis I, Ch. Ulrichs (2001), J. Stored Prod. Res. 37. pp. 153-164. Action of amorphous diatomaceous earth against different stages of the stored product pests *Triboliumconfusum, Tenebriomolitor, Sitophilusgranarius* and *Plodiainterpunctella* are also disclosed.

Reference may also be made to Studies on plant oils as surface protectant against pulse beetle *Callosobruchus chinensis* (L.) in chickpea, *Cicer arietinum* L. [Singal, S. K. and Singh. Z, 1990, Tropical Pest Management, 36.314-316] wherein the traditional practice of mixing stored grain with vegetable oils is documented. However, the drawbacks are that the oils apart from being expensive also turn rancid and may impart an off-flavour to the grain as shown by Pereira, J. and Wholgemuth, R. 1983, J. Stored Prod. Res. 19, 57-62. The effect of six vegetable oils as protectants of cowpeas and Bambara groundnut against infestation by *Callosobruchus maculatusis* also reported.

References may be made to Journals Efficacy of deltamethrin against storage insects in rice and wheat under FCI's storage system. (Pesticides pg 39-43) and toxicity of deltamethrin, chlorpyriphos, methyl etrifos, malathion and fluvalinate against *Sitophilus oryzae* and *Trogoderma granarium*. Ind. J. Ent. 56(4). 322-325 by Yadav et al., wherein the organophosphate insecticide DDVP is used in insecticide formulations along with malathion for the control of insect pests in grain storage. However, insects have become resistant to DDVP and malathion and these are being phased out. DDVP is known to be carcinogenic. Currently, while malathion is being replaced with deltamethrin, there is no replacement for DDVP which acts in the vapor phase.

References may be made to patents IN192851 and IN199867 by Pereira et. al. describe a process for the preparation of a formulation useful for the insect free storage of cereals using roots of *Decalepis hamiltonii* Wight. and Arn. and its extracts mixed with substituted phenols wherein substituted phenols were mixed with the dried root powder/solvent extracts of the roots of *Decalepis hamiltonii* to provide a stable, synergistic formulation for the storage of insect free cereals. However, the formulation is not effective against the red flour beetle, *Tribolium castaneum* Herbst. There is need to develop new insecticides of biological origin (biopesticides) that are biodegradable and do not leave residues, which are also species specific and do not harm non target organisms.

*Nothapodytes nimmoniana* (Syn: *N. foetida, Mappia foetida*) (Family: Icacinaceae) is gaining international importance due to their pharmacological and curative properties. The wood-extract of this tree is used in the treatment of cancer. It is believed that Camptothecin (CPT) is the third most important alkaloid sought after by the pharmaceutical companies around the world. Few developments on pesticide/herbicide and insecticidal properties of *Nothapodytes nimmoniana* extracts are enlisted in below references:

References may be made to patent JP61200902, provides a novel herbicide containing 9-methoxycamptothecin, etc., extracted from vegetables as active components, exhibiting excellent herbicidal effect to various weeds and free from phototoxicity to important crops such as corn, wheat, rice, soybean, cotton, etc. The said herbicide contains, as active component, 9-methoxycamptothecin separated from *Mappia foetida* (a plant of Icacinaceae family) and reported to have carcinostatic and antileukemic activities, or an extract containing 9-methoxycamptothecin extracted from a plant.

The extraction of the above active component is carried out by conventional process for the extraction of natural component, e.g. by the extraction with an organic solvent such as methanol, acetone, ethyl acetate, etc., following concentration, etc. The herbicide is effective against broad-leaved weeds such as white-bird's-eye, smooth pigweed, green amaranth, etc., gramineous weeds such as barnyard grass, green foxtail, etc., cyperaceous weeds such as yellow-cyperus, etc.

References may be made to U.S. Pat. No. 6,893,668 (corresponding Indian Patent Application No. 746/DEL/2003) provides a process for the isolation of Camptothecin from the twigs and stem of *N. foetida*, which comprises of drying, grinding *N. foetida* twigs and stems, subjecting the dried and ground *N. foetida* twigs and stems to hot defatting with a light petroleum fraction followed by successive sequential hot extraction with two solvents, removing the solvents under vacuum to obtain crude extracts of the plant material, precipitating and filtering the crude plant extracts to obtain Camptothecin with up to 0.15% yield.

References may be made to patent CN101243796 (WO2009/111950) which relates to a composition of pesticide and the manufacturing method, belonging to botanical pesticide which is characterized in that the composition comprises an active constituent with 0.1 to 2.0 percent of the total weight. The constituent is single compound or the mixture of compounds which accords to the general formula I, wherein $R_1$ is Na and $R_2$ is H or OH.

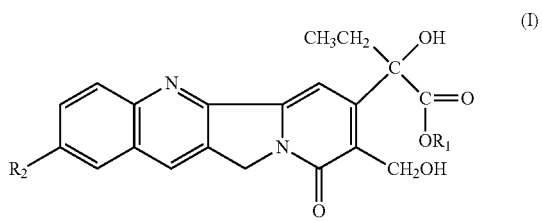

(I)

The composition of pesticide adopts the ring opening camptothecin salt as the insecticidal active compound, wherein, the camptothecin salt is high in activity and can be dissolved in water.

References may be made to patent US20020018762 relates to insect control with *Camptotheca* products, particularly, termiticides, baits, preservatives, and termite-resistant products. Natural or synthetic Camptothecin and/or one of its natural or synthetic analogs are applied to deter and/or eliminate termites, while flavonoids are applied to attract termites. CPTs and/or CPTs-containing plant matter is processed with cellulose products to produce termite-resistant products and structures.

Further "Insecticidal Activity of Camptothecin against *Nilaparvata lugens, Brevicoryne brassicae*, and *Chilo suppressalis*" by Jianyi Ma, et. al. discloses that greenhouse tests showed that 0.2% Camptothecin Emulsifiable Concentrate (EC) has strong contact toxicity to three agricultural pests in the following descending order *Nilaparvata lugens* Stahl, *Brevicoryne brassicae* L., *Chilo suppressalis* Walker.

Camptothecin isolated from the stem of *Nothapodytes foetida* is known to possess anti-cancer properties, which is currently in demand for anticancer treatment. Therefore, the present inventors have evaluated the *Nothapodytes foetida* stem extract that is substantially free from camptothecin for its other biological activities and surprising found that the stem extract of *Nothapodytes foetida* is found to be an effective biopesticide for the insect free storage of stored grain and seed.

Accordingly, the present inventors have developed a biopesticide from the stem of *Nothapodites foetida*, that can be used to protect stored grain/seed and also store organically produced grain/seed from insect infestation. The said biopesticide being of biological origin is eco-friendly and less toxic to non-target organisms.

OBJECTIVE OF THE INVENTION

Main objective of the present invention is to provide insecticidal compound of general formula 1 and formula 2 isolated from the stem of *Nothapodites foetida* (Wight.) Sleumer (formerly *Mappia foetida* (Miers)) useful for the insect free storage and transport of grains and seed.

Another objective of the present invention is to provide insecticidal enriched extract isolated from the stem of *Nothapodites foetida* (Wight.) Sleumer.

Another objective of the present invention is to provides insecticidal activity of the enriched extract (biopesticide) of the invention, ascribed due to compound/s other than camptothecin.

SUMMARY OF THE INVENTION

Accordingly, present invention provides compound of general formula 1 and formula 2

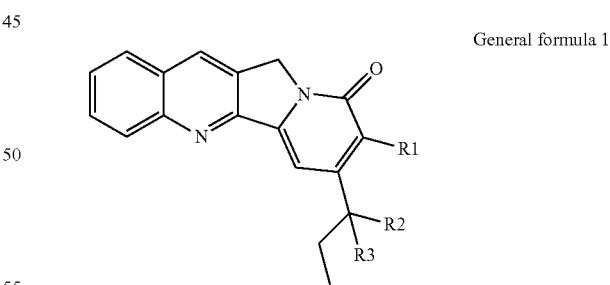

General formula 1 wherein $R1=CH_3$, $CH_2OAc$ and wherein $R2=COOH$, or

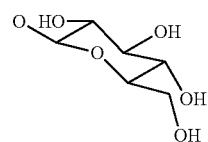

and $R3=H$, $OH$.

Formula 2

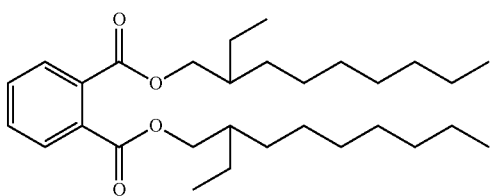

In an embodiment of the present invention, representative compounds of general formula 1 comprising following compounds:

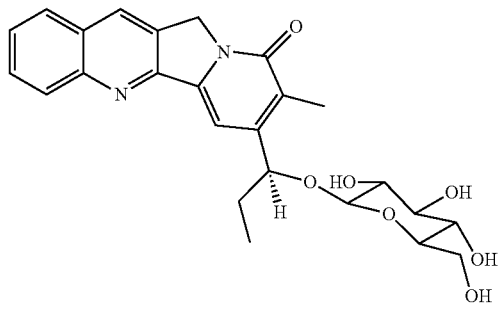

Camptothecanoid-1 (D3)

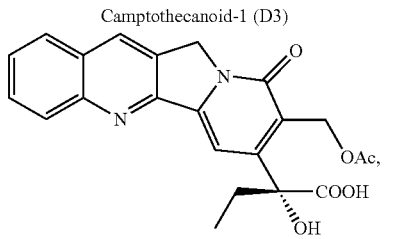

Camptothecanoid-2 (CPT D5: R = H)

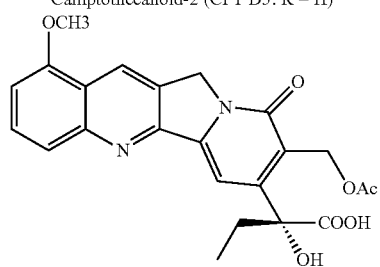

Camptothecanoid-3 (CPT D6: R = OMe)

In another embodiment of the present invention, said compounds are useful for the protection of stored grains and seed from insect infestation.

Yet another embodiment of the present invention, the said compounds are non-toxic to non-target insect pests like aphids, *thrips*, diamondback moth, tobacco caterpillar, gram pod borer, bihar hairy caterpillar, potato tuber moth, tea mosquito, red spider mite and Mexican beetle.

Yet another embodiment of the present invention, the said compounds are active against stored product insect pests namely the red flour beetle, *Tribolium castaneum*, lesser grain borer, *Rhizopertha dominica*, pulse beetle, *Callosobruchus chinensis*, almond moth, *Ephestia cautella*, rice moth, *Corcyra cephalonica*.

Yet another embodiment of the present invention, Insecticidal composition comprising compound of general formula 1 or 2 either alone or in combination thereof optionally along pharmaceutically acceptable additives useful for the protection of stored grains and seed from insect infestation.

Yet another embodiment of the present invention, the additives are selected from the group consisting of diluents, solvents, surfactants and carriers.

Yet another embodiment of the present invention, the said composition is in the form of spray, dust, powder, tablet and pellets.

Yet another embodiment of the present invention, the said composition is effective for more than 100 days with a reduction in F1 progeny of the infestants.

Yet another embodiment of the present invention, the said composition exhibits 100% mortality of rice weevil *Sitophilus oryzae*, lesser grain borer *R. dominica* and *Callosobruchus chinensis*.

Yet another embodiment of the present invention, process for the preparation of compounds of general formula 1 and formula 2 from the stem of *N. foetida* comprising the steps of:

i. drying the stem of the *Nothapodites foetida* in shade followed by cutting into small pieces and pulverizing;
ii. extracting the powder of step [i] with methanol and designating the extract as S1;
iii. extracting the residue of step [ii] with methanol and designating the extract as S2;
iv. extracting the residue of step [iii] with methanol and designating the extract as S3;
v. stripping off methanol from extracts 1, 2 and 3 as obtained in step (ii) (iii) and (iv) respectively, pooling and defatting the residue in petroleum ether;
vi. optionally, combining the extracts 1, 2 and 3 as obtained in step (ii), (iii) and (iv) respectively to yield an extract designated as S4;
vii. stripping off methanol from extract 4 as obtained in step (vi) followed by defatting thereof in petroleum ether to obtain extract S5 and defatted residue S6;
viii. partitioning the defatted residues S6 as obtained in step [v] and/or [vii] in n-butanol designated as S7 and in water designated as S8;
ix. stripping off the solvent to obtain the insecticidal enriched bioactive extract;
x. removing camptothecin by column chromatography (CC) to obtain fraction D1-D26;
xi. subjecting fraction D1-D26 to CC using successively methyl cynate and chloroform (2:8) and then gradient of methanol and chloroform to obtain D24, D25, D18, D21 and D4;
xii. subjecting fraction D18, D21 and D4 to CC as obtained in step (xi) in gradient of MeCN:chloroform to obtain fraction D18:2, D21:2 and D4:2 contained pure phthalate of general formula 2;
xiii. separating fraction D24 as obtained in step (xi) using gradient of methanol in chloroform followed by methanol wash to obtain fraction D24:12 contained compound campptothecanoid 1 of general formula 1;
xiv. separating fraction D25 as obtained in step (xi) using gradient of methanol in chloroform to obtain fraction D25:4-5 contained compounds camptothecanoids 2 and 3 of general formula 1.

DETAILED DESCRIPTION OF THE INVENTION

Figure 1:
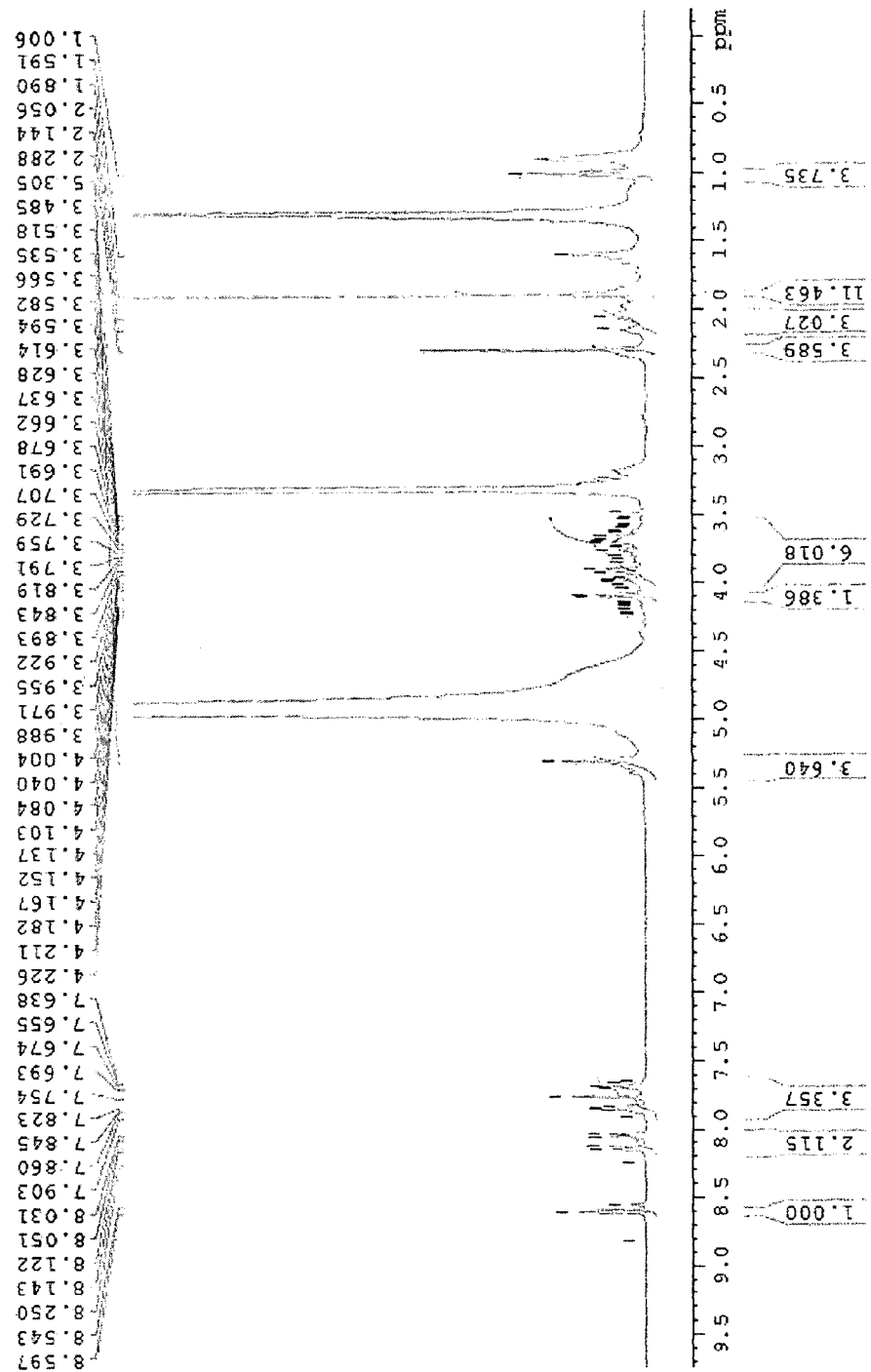
FIG. 1 represents $^1$H NMR of camptothecanoid 1.
Figure 2:
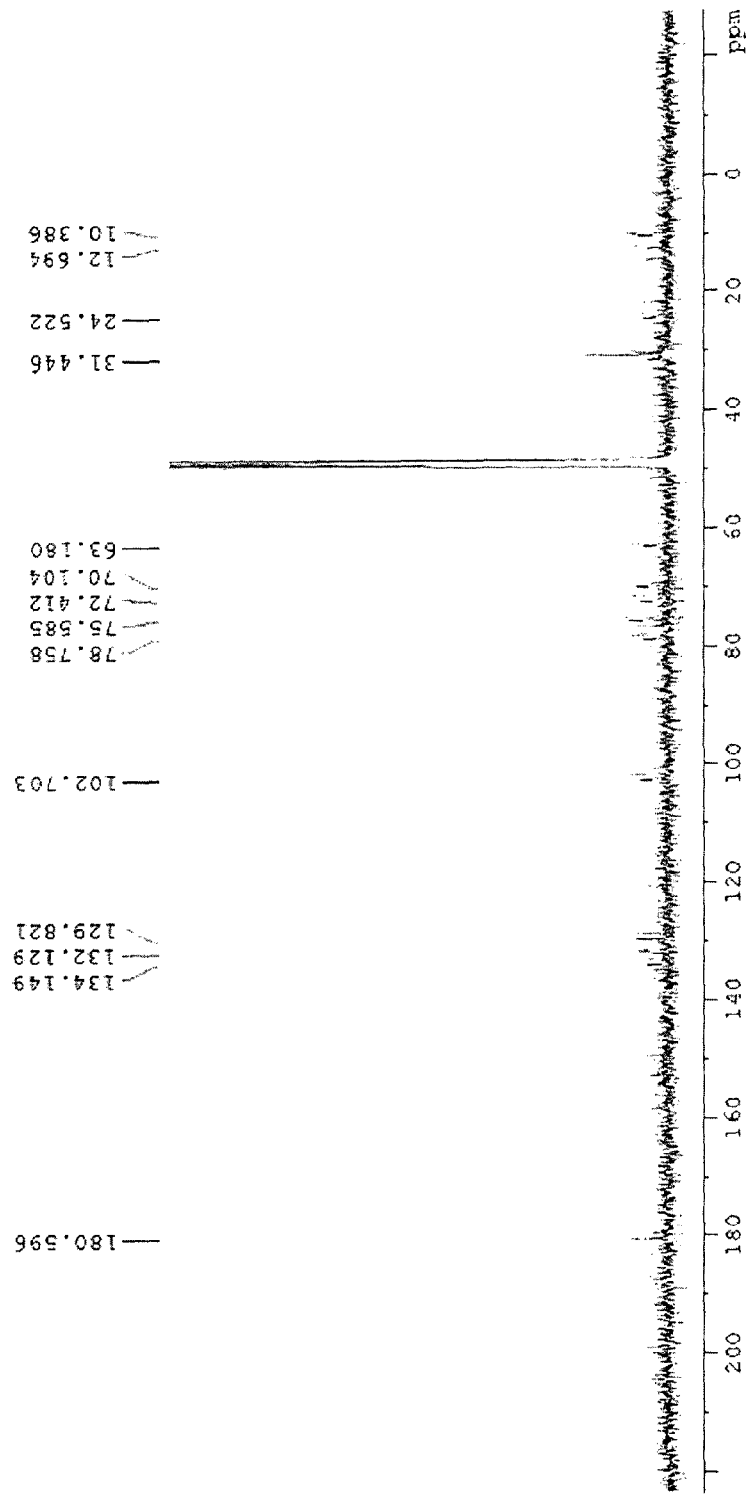
FIG. 2 represents $^{13}$C NMR of camptothecanoid 1.
Figure 3:
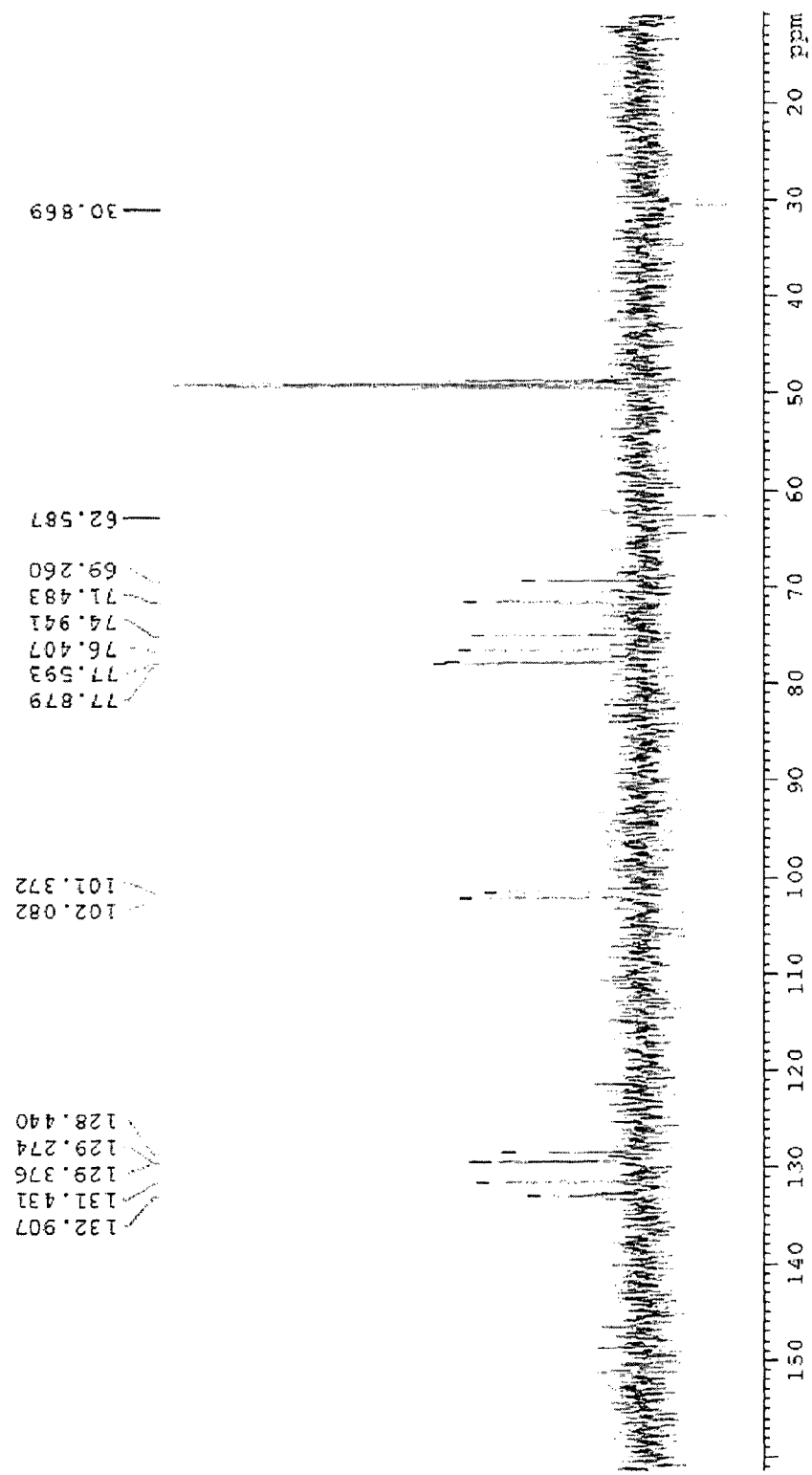
FIG. 3 represents Distortionless Enhancement by Polarization Transfer (DEPT) of camptothecanoid 1.
Figure 4:
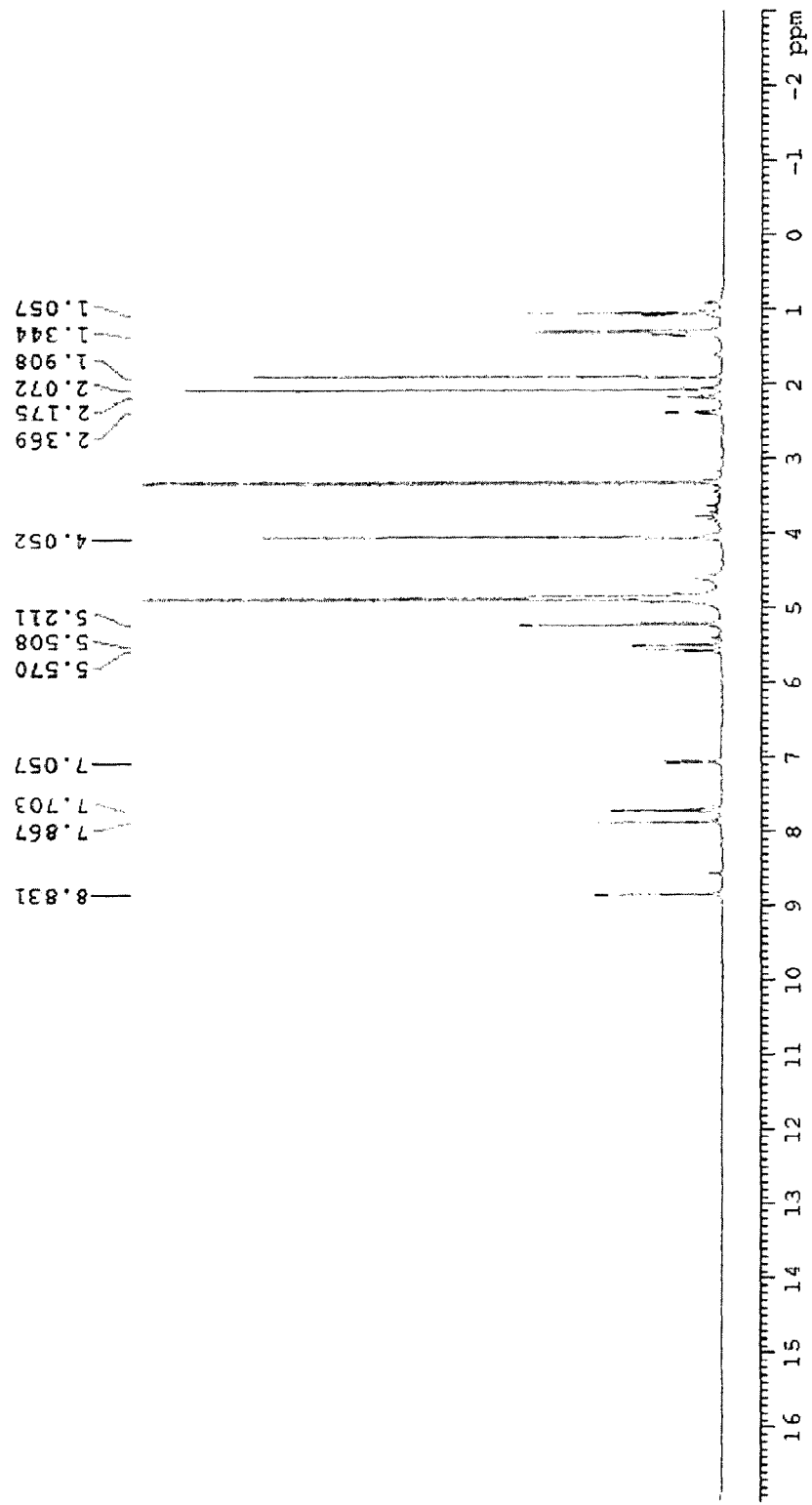
FIG. 4 represents $^1$H NMR of camptothecanoid 2.
Figure 5:
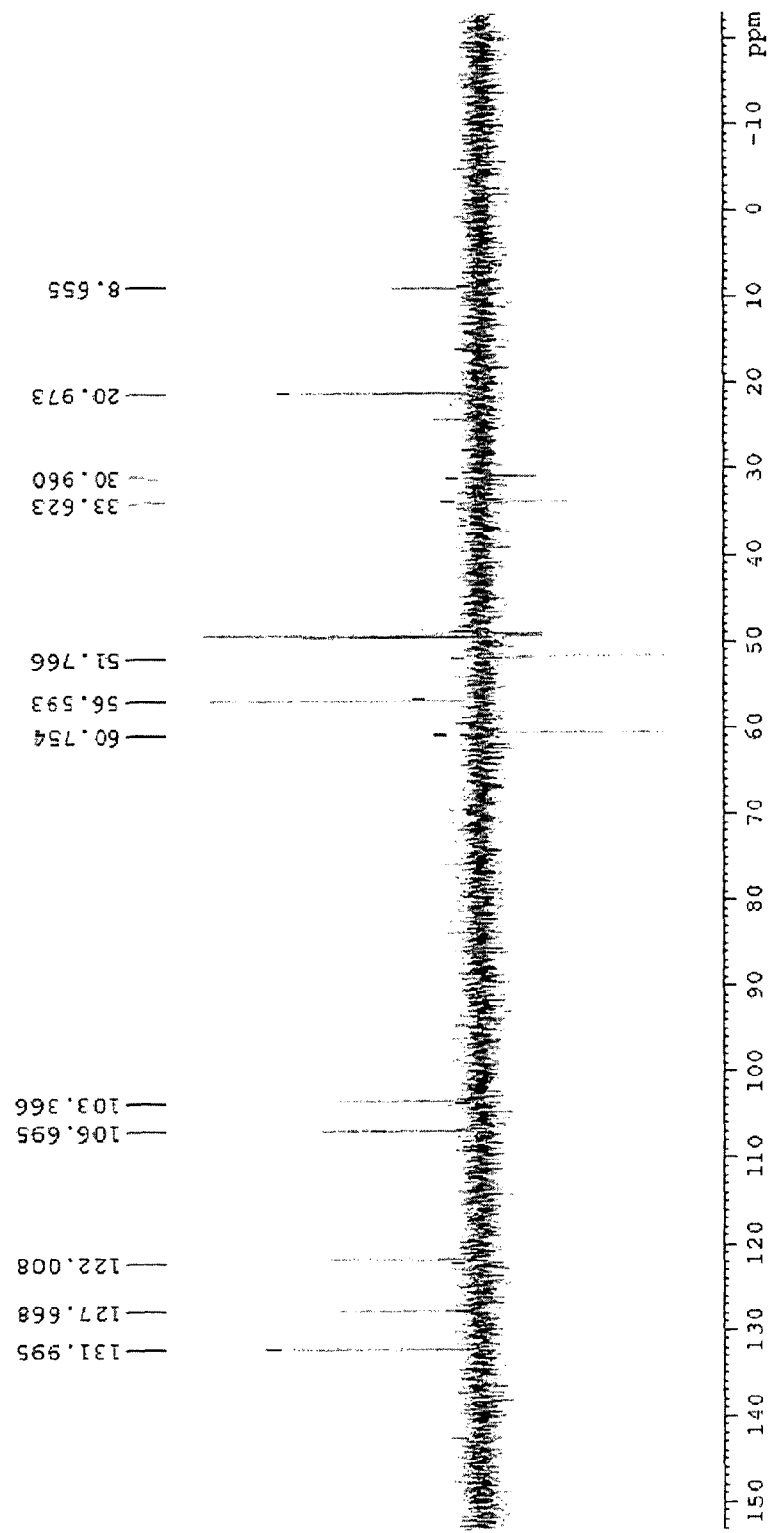
FIG. 5 represents DEPT of camptothecanoid 2.
Figure 6:
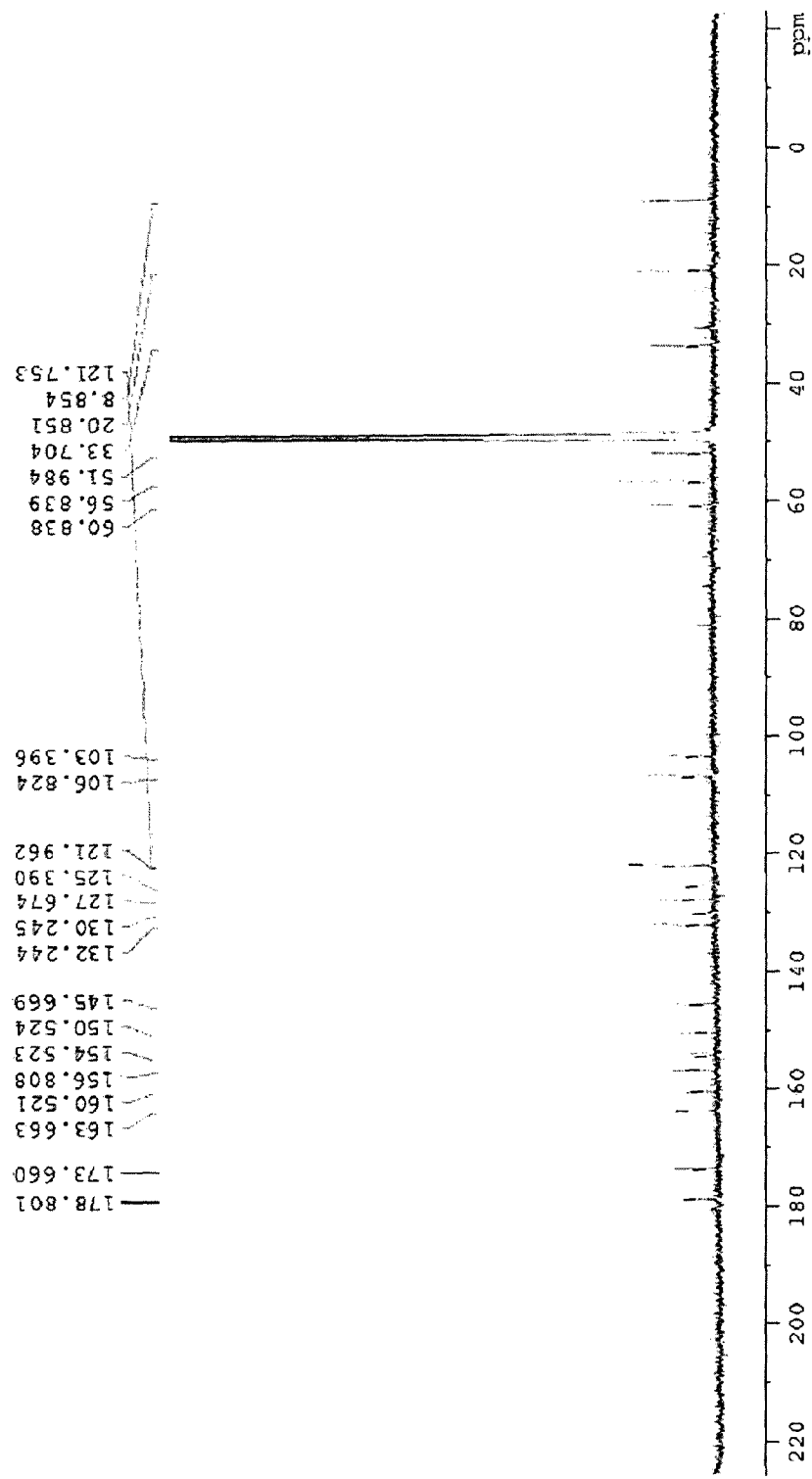
FIG. 6 represents $^{13}$C NMR of camptothecanoid 2.
Figure 7:
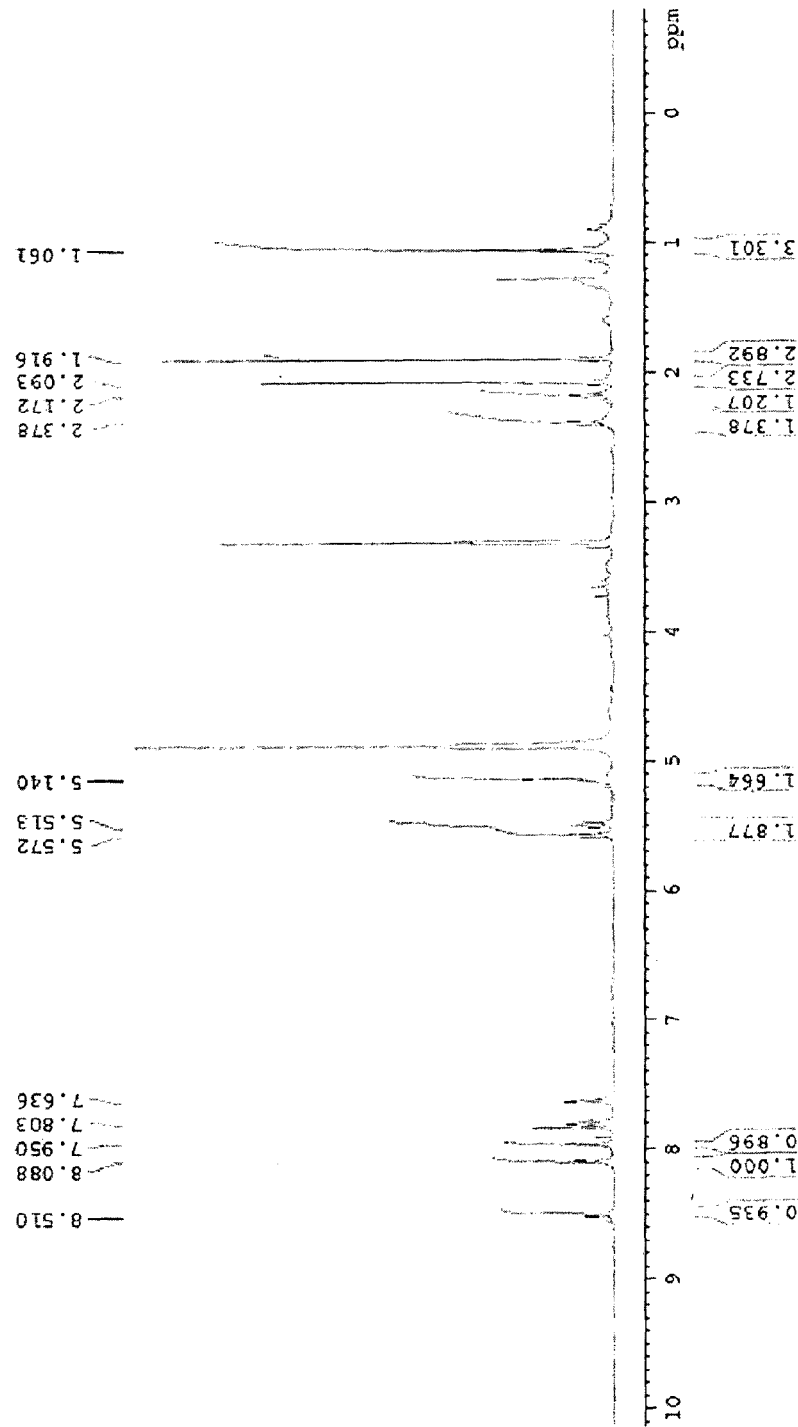
FIG. 7 represents $^1$H NMR of camptothecanoid 3.
Figure 8:
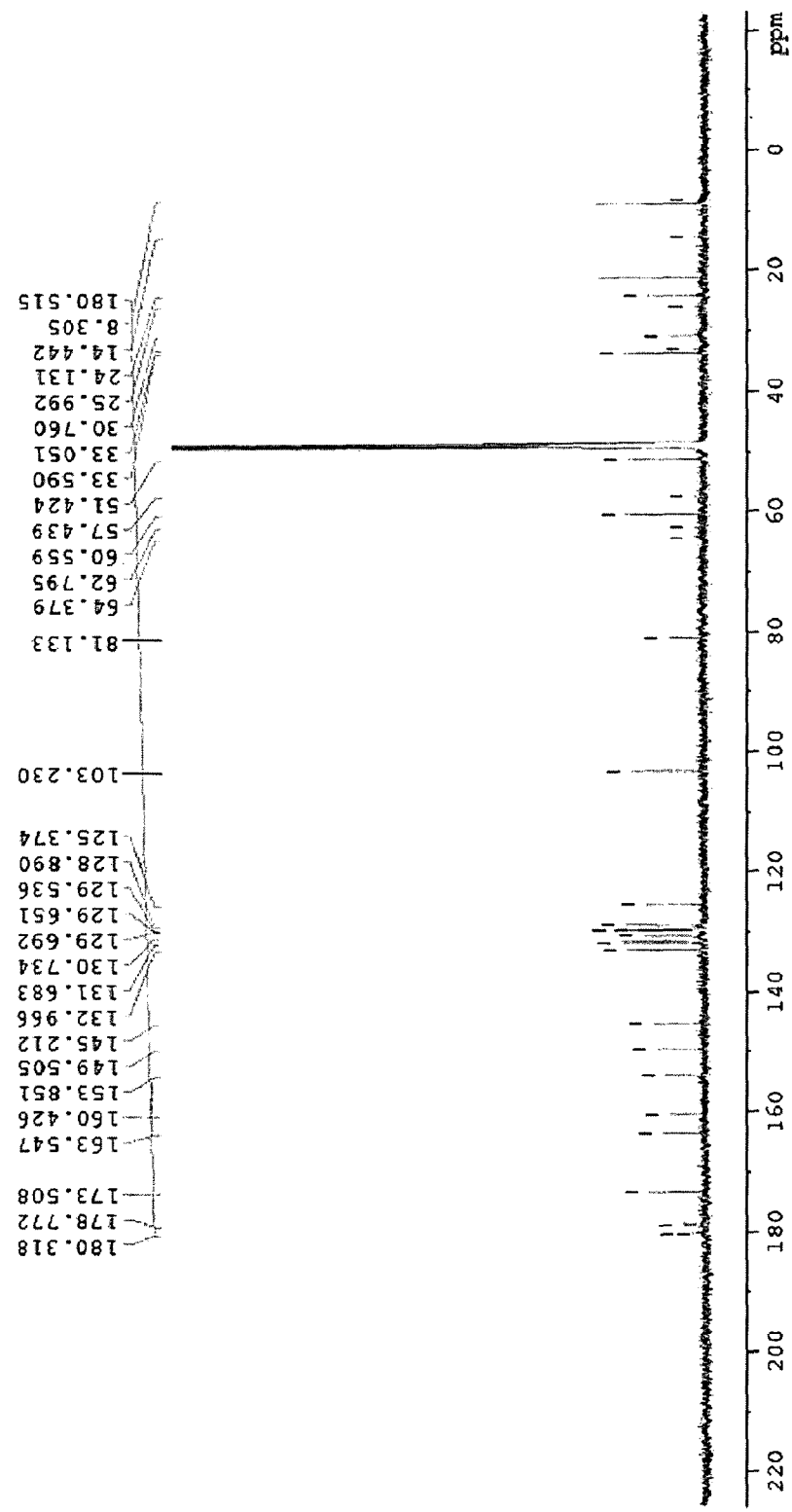
FIG. 8 represents $^{13}$C NMR of camptothecanoid 3.
Figure 9:
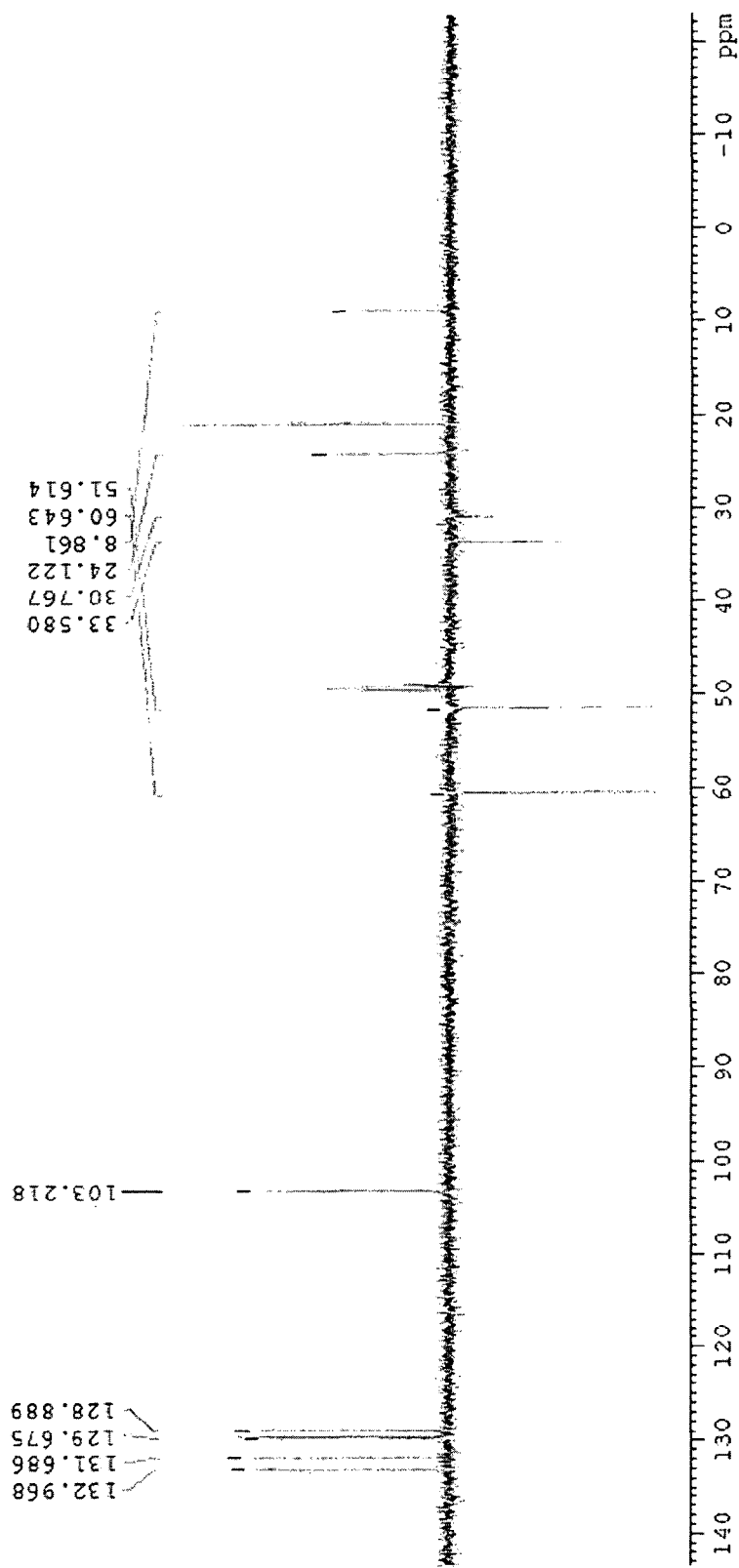
FIG. 9 represents DEPT of camptothecanoid 3.
Figure 10:
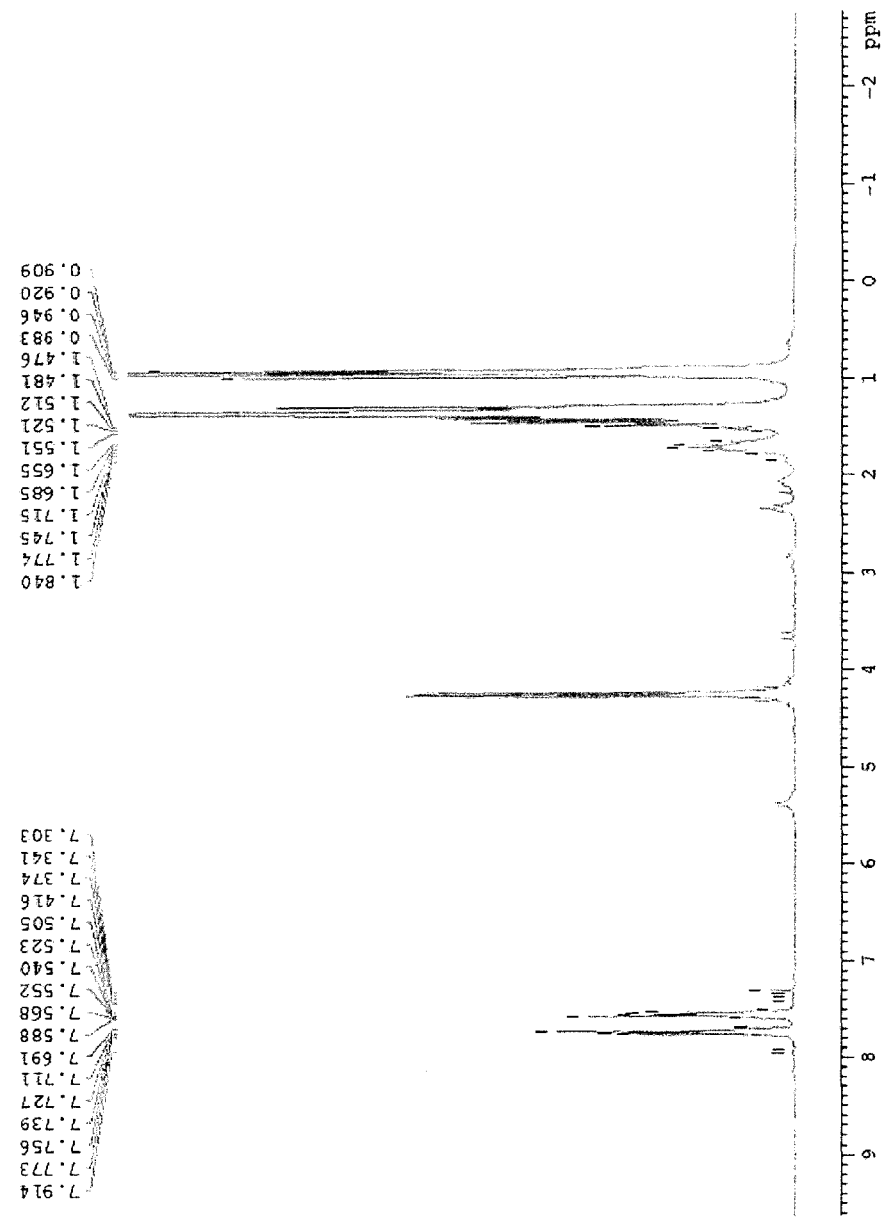
FIG. 10 represents $^1$H NMR of Phthalate.
Figure 11:
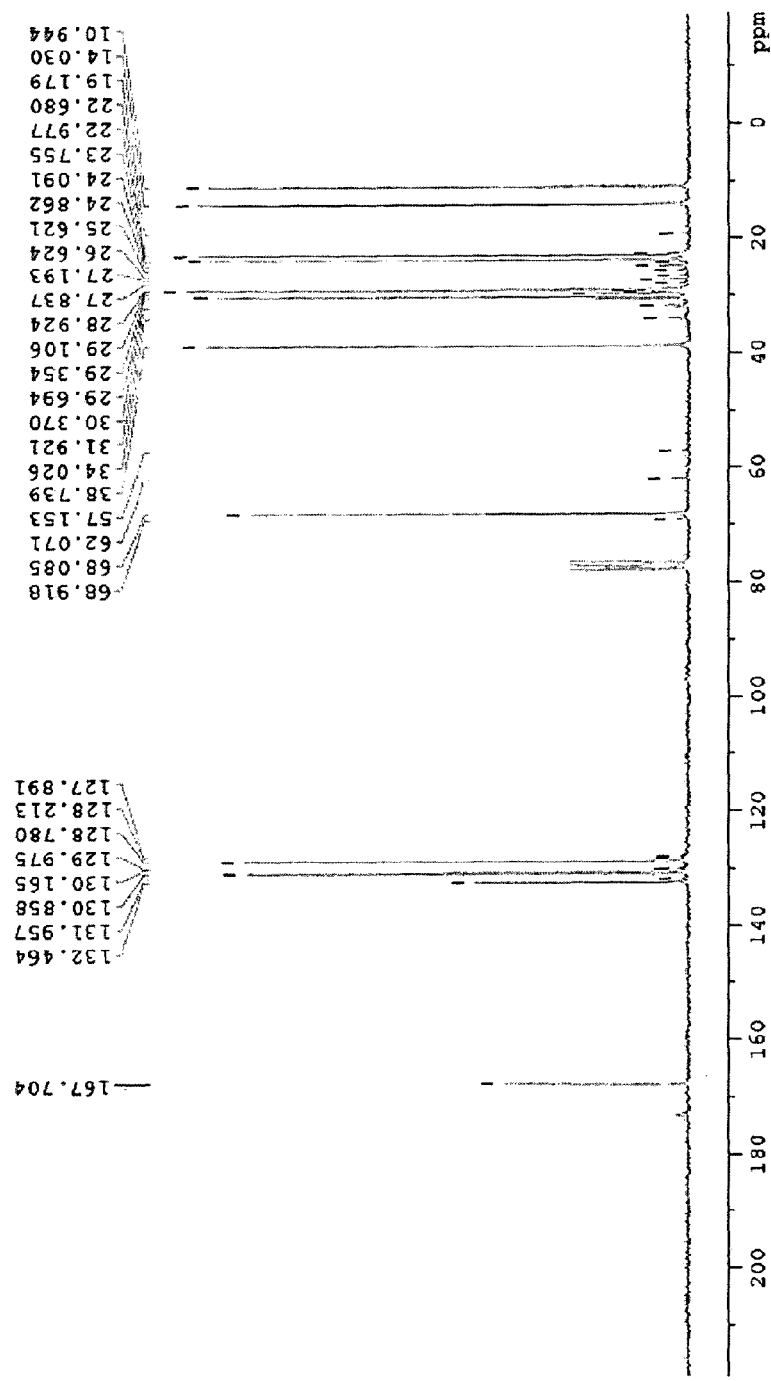
FIG. 11 represents $^{13}$C NMR of Phthalate.
Figure 12:
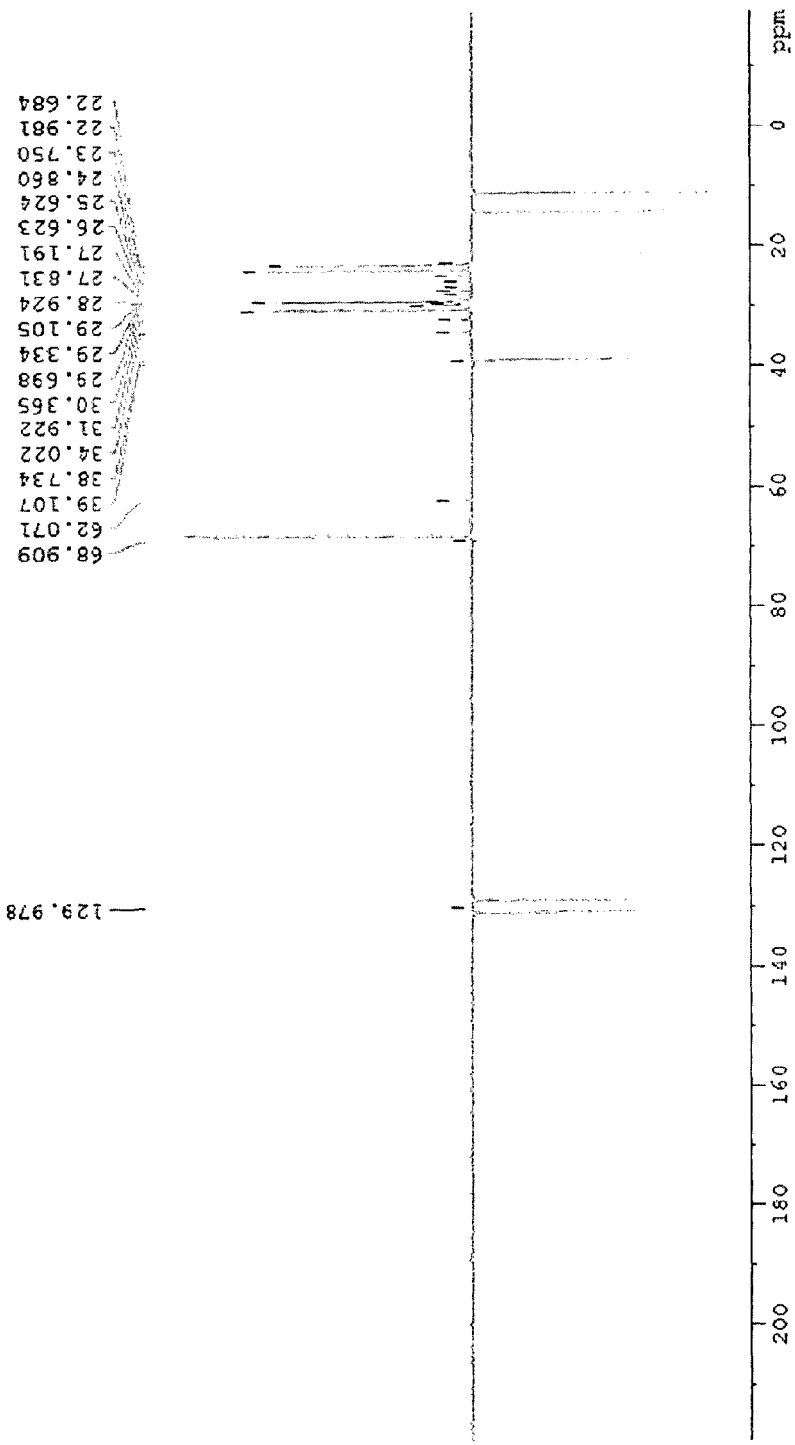
FIG. 12 represents DEPT of Phthalate.

The present invention describes insecticidal activity of compound of general formula 1 isolated from the stem of *Nothapodites foetida*, containing compound/s substantially free from camptothecin that is used to protect stored and under transit grain/seed and also to store and transport organically produced grain/seed from insect infestation.

The insecticidal enriched extract (biopesticide) from the stem of *Nothapodites foetida*, containing compound/s other than camptothecin that is used to protect the grains during transport also.

The biopesticide compound of general formula 1 and formula 2 described in the current invention is non-toxic to non-target insect pests and active against stored product insect pests namely the red flour beetle, *Tribolium castaneum*, lesser grain borer, *Rhizopertha dominica*, pulse beetle, *Callosobruchus chinensis*, almond moth, *Ephestia cautella*, rice moth, *Corcyra cephalonica*; and not active against aphids, *thrips*, diamondback moth, tobacco caterpillar, gram pod borer, Bihar hairy caterpillar, potato tuber moth, tea mosquito, red spider mite, Mexican beetle. Thus, the insecticidal extract is specific to the stored product insect pests.

The insecticidal enriched extract (biopesticide) using wheat treatment technique (defined in example 1) is found to give 100% mortality of rice weevil *Sitophilus oryzae* and lesser grain borer *Rhizopertha dominica*. The treatment is found to be effective for more than 100 days with a reduction in F1 progeny. In yet another aspect, the active insecticidal enriched extract is formulated into a free flowing dust formulation with the addition of inactive additives like diluents, solvents, surfactants and carriers. The dust formulation is used to protect stored wheat from insect attack for more than 6 months causing 100% insect mortality and reduced F1 progeny. (first generation of insects.)

The insecticidal activity of the extract is attributed to its low camptothecin concentration and the other contents of the extract.

The pulverized stem is extracted from methanol, 1:1 methanol:water and water to detect the insecticidal activity of the extracts and found that the methanolic extract is found to be good over hydro-methanolic extract and water extract. Due to this, present invention discloses a process for preparation of insecticidal enriched extract (biopesticide) from the stem of *Nothapodites foetida*, which comprises;
1. Extracting the dried stem powder repeatedly with methanol only;
2. Stripping off methanol from all the combined extract and then extracting residue in Petroleum ether to remove fatty material;
3. Partitioning the residue from the above step with n-butanol and water; and
4. Stripping off the n-butanol solvent to obtain the insecticidal enriched extract;
5. Isolating compound of general formula 1 and formula 2 from insecticidal enriched extract

Definitions and Abbreviations

CPT: Camptothecin
S1: Methanol extract of powder.
S2: Methanol extract of residual powder after removal of S1.
S3: Methanol extract of residual powder after removal of S2.
S4: Combined methanol extracts (S1+S2+S3) contains 0.262% of CPT.
S5: Pet ether extract of S4 containing the fatty fraction and devoid of CPT. Labeled as S4-A in bioassays.
S6: Defatted fraction of S4 i.e. residue of S4 after extraction with Pet ether Labeled as S4-B containing 0.272% CPT.
S7: n-butanol soluble fraction of S6 i. e. S6 was separated in n-butanol:water Labeled as S4-B1 containing 1.168% CPT.
S7A from S1 directly (% Camptothecin: 5.0763)
S7B from S2 directly (% Camptothecin: 6.037)
S7C from S3 directly (% Camptothecin: 3.849)
S8: Water soluble fraction of S6 separated from n-butanol fraction as explained in S7 containing devoid of CPT.
S4—Methanol extract (with 4.89% camptothecin)
T1—Methanol:water (1:1) extract
T2—Water extract
"Substantially Free of Camptothecin" refers to the extract containing less than about 12.5 ppm of the Camptothecin content. Preferably, 10 ppm of the Camptothecin content. More preferably the 5 ppm.
F1 Progeny refers to first generation of insects.
Progeny/adult day refers to generation.

EXAMPLE

The following examples are given by way of illustration therefore should not construed to limit the scope of the invention.

Example 1

The stem of the *Nothapodites foetida* plant material was shade dried, cut into small pieces and pulverized. The powder was extracted in three solvent systems and the extracts labeled as follows:

| Solvent system | Extract |
| --- | --- |
| Methanol | S4 |
| Methanol:water (1:1) | T1 |
| Water | T2 |

The bioefficacy of the extracts were screened against *S. oryzae* and *R. dominica* on wheat at 1000 ppm. Required quantity of the extract dissolved in 6 ml of the solvent was pipetted over 60 gm wheat, taken in a 500 ml beaker. The grain was stirred with a glass rod to obtain uniform application. The control grain received the solvent alone. The treated grain was spread on petridish and kept overnight (12 hrs) for the solvent to evaporate. The 60 gm grain was divided into three lots of 20 gm each, taken in test tubes 25 mm diameter and 95 mm long.

Fifteen unsexed adults, 1-2 weeks old, of the rice weevil, *Sitophilus oryzae* and the lesser grain borer, *Rhizopertha dominica* were seeded into the tubes separately. The tubes were covered with muslin held by rubber bands. The mortality of the test insects was recorded after 1, 3, 7, 14 and 21 days. After the last count, the insects were discarded and the grain incubated to obtain the F1 progeny. The number of emerging progeny was recorded every second day till the emergence was complete. The progeny/adult day was calculated by Kazmaier et. al method. The progeny/adult day corrects for the reduction in the number of progeny due to adult mortality. A significant reduction in the progeny/adult day compared to the control indicates Insect Growth Regulating (IGR) activity, which is presented in Tables 1, 2 and 3.

TABLE 1

Bioefficacy of Nothapodites foetida extracts against S. oryzae

| | | Progeny/adult day | |
|---|---|---|---|
| | % mortality | Control | Treated |
| S4 | 74 | 0.855 | 0.016 |
| T1 | 42.43 | 0.855 | 0.034 |
| T2 | 00.00 | 1.030 | 0.660 |

TABLE 2

Bioefficacy of Nothapodites foetida extracts against R. dominica

| | | Progeny/adult day | |
|---|---|---|---|
| | % mortality | Control | Treated |
| S4 | 53.33 | 0.785 | 0.020 |
| T1 | 44.00 | 0.785 | 0.033 |
| T2 | 36.00 | 0.939 | 0.184 |

Conclusion: The extract S4 was the most active against both the tested insects.

TABLE 3

Bioefficacy of Nothapodites foetida extracts against C. chinensis

| Treatment | Avg. No. of Progeny* |
|---|---|
| Solvent Control | 101.75 |
| S4 | 00.00 |
| T1 | 02.25 |

*Average of four replicates.

Avg. No. of Progeny is average number of individuals emerged while Progeny/adult day is a ratio term. From Tables 1, 2 and 3, it is seen that all the three extracts were active. Apart from adult mortality, there was a significant reduction in the progeny/adult day indicating a strong Insect Growth Regulating activity (IGR) of the three extracts and S4 was found to be the most active extract.

Example 2

The stem of the plant material was shade dried, cut into small pieces and pulverized. Since, methanol was the best solvent of the three solvent systems assayed, the powder was extracted with methanol and designated as Extract 1 (S1). The residual powder was extracted again with methanol and the extract designated as Extract 2 (S2). The residual powder was extracted again with methanol and the extract designated as Extract 3 (S3).

All the three extracts were stripped of methanol individually (S4) and the residue extracted in petroleum ether (S5) to remove the fatty material present in the extracts.

The defatted residue (S6) was partitioned in n-butanol and water. The n-butanol fraction (S7) was stripped of the solvent to obtain:

S7A from S1 directly (% Camptothecin: 5.0763)
S7B from S2 directly (% Camptothecin: 6.037)
S7C from S3 directly (% Camptothecin: 3.849)

These three fractions were assayed against S. oryzae and R. dominica as in Example 1. The results are presented in Table 4.

TABLE 4

Bioefficacy of fractions S7A, S7B and S7C against S. oryzae and R. dominica

| | | % mortality* | | No. adults emerged | |
|---|---|---|---|---|---|
| Treatment | (ppm) | S. oryzae | R. dominica | S. oryzae | R. dominica |
| Blank control | 00 | 00.00 | 00.00 | 212 | 171 |
| S7A | 50 | 11 | 43 | 00 | 00 |
| S7B | 50 | 29 | 37 | 00 | 00 |
| S7C | 50 | 46 | 46 | 00 | 00 |
| S7A | 100 | 39 | 59 | 00 | 00 |
| S7B | 100 | 63 | 76 | 00 | 00 |
| S7C | 100 | 55 | 65 | 00 | 00 |
| S7A | 200 | 77 | 84 | 00 | 00 |
| S7B | 200 | 86 | 91 | 00 | 00 |
| S7C | 200 | 100 | 100 | 00 | 00 |
| S7A | 500 | 100 | 100 | 00 | 00 |
| S7B | 500 | 100 | 100 | 00 | 00 |
| S7C | 500 | 100 | 100 | 00 | 00 |

*% mortality at the end of 21 days. With 200 and 500 ppm, 100% mortality was obtained within 14 days.

Fraction S7C contained 3.85% Camptothecin as determined by HPLC. Fraction S7C at 50 ppm and 100 ppm on wheat would be equivalent to 1.993 ppm and 3.986 ppm of Camptothecin respectively.

Camptothecin obtained from Sigma Aldrich was assayed on wheat against S. oryzae and R. dominica as in example 1. The results are presented in table 5.

TABLE 5

Bioefficacy of Camptothecin treated on wheat against rice weevil, Sitophilus oryzae and lesser grain borer, Rhizopertha dominica.*

| Treatment (ppm) | Mortality (%) | No. days for 100% kill | No. of F1 progeny |
|---|---|---|---|
| 100 | 100 | 3 | 00 |
| 75 | 100 | 7 | 00 |
| 50 | 100 | 14 | 00 |
| 25 | 100 | 21 | 00 |
| 12.50 | 00 | — | 00 |
| 6.25 | 00 | — | 00 |

At 12.50 ppm, there was no adult mortality but 100% inhibition of F1 progeny. However, with fraction S7C at 100 ppm and 50 ppm equivalent to 3.986 ppm and 1.993 ppm respectively of Camptothecin, there was adult mortality and 100% inhibition of F1 progeny with S. oryzae.

From the above experiment, it can be concluded that there is/are toxic principle/s in the extracts other than Camptothecin, that is/are acting as effective components of biopesticide/s over camptothecin.

Example 3

Fraction S7A as obtained in example 2 was separated by column chromatography using silica gel as stationary phase and methanol:chloroform gradient as mobile phase into 6 fractions designated as E1, E2, E3, E4, E5 and E6. The six fractions as obtained were assayed on wheat against S. oryzae and R. dominica as described in example 1. The results are presented in Table 6 and Table 7.

TABLE 6

Bioefficacy of S7A fractions against rice weevil, *Sitophilus oryzae*

| Fraction | % CPT | 25 ppm (in brackets, amount of CPT in ppm is reported) | | 50 ppm | | 100 ppm | | 200 ppm | |
|---|---|---|---|---|---|---|---|---|---|
| | | % mort. | Avg. No. emerge | % mort. | Avg. No. emerged | % mort. | Avg. No. emerged | % mort. | Avg. No. emerged |
| E1 | 0.1542 | | | | | | | | |
| E2 | 18.8903 | 18.3 (4.72) | 35 | 96.6 (9.44) | 7.5 | 98.3 (18.88) | 7.0 | 95 (37.76) | 4.7 |
| E3 | 3.1209 | 8.3 (0.78) | 79 | 18.3 (1.56) | 51.5 | 18.3 (3.12) | 20.5 | 18.3 (6.24) | 13.2 |
| E4 | 0.1409 | 5.0 (0.035) | 114 | 3.3 (0.07) | 115 | 5.0 (0.14) | 119 | 5.0 (0.28) | 92 |
| Control (solvent control for E1 to E4) | | 1.6 | 145 | 1.6 | 145 | 1.6 | 145 | 1.6 | 145 |
| E5 | 0.0330 | 8.3 (0.008) | 150 | 5.0 (0.016) | 135 | 5.0 (0.032) | 125 | 5.0 (0.064) | 136 |
| E6 | 0.6430 | 3.3 (0.161) | 129 | 1.6 (0.232) | 120 | 5.0 (0.464) | 121 | 5.0 (0.928) | 83 |
| Control (water control for E5 and E6) | | 1.6 | 172 | 1.6 | 172 | 1.6 | 172 | 1.6 | 172 |

TABLE 7

Bioefficacy of S7A fractions against lesser grain borer, *Rhozopertha dominica*

| Fraction | 25 ppm | | 50 ppm | | 100 ppm | | 200 ppm | |
|---|---|---|---|---|---|---|---|---|
| | % mort. | Avg. No. emerged | % mort. | Avg. No. emerged | % mort. | Avg. No. emerged | % mort. | Avg. No. emerged |
| E1 | | | | | | | | |
| E2 | 75.0 | 4.7 | 81.6 | 0.0 | 90 | 0.0 | 91.6 | 0.0 |
| E3 | 20.0 | 1.25 | 23.3 | 0.5 | 18.3 | 0.75 | 33.3 | 0.0 |
| E4 | 65.0 | 12.0 | 71.6 | 3.7 | 81.6 | 4.5 | 95.0 | 3.2 |
| E5 | 11.6 | 30 | 10.0 | 23.2 | 11.6 | 26.2 | 15.0 | 15.5 |
| E6 | 11.6 | 18 | 100 | 2.7 | 90.0 | 0.2 | 95.0 | 0.5 |
| Control | 3.3 | 74.3 | 3.3 | 74.3 | 3.3 | 74.3 | 3.3 | 74.3 |

All the fractions exhibited toxicity to the test insects and there was a significant reduction in progeny.

Example 4

Fraction E4 and E6 as obtained in example 3 were further fractionated by preparative HPLC using RP-18 column and acetonitrile:water gradient as mobile phase for E4 and methanol:water gradient for E6 into 5 and 4 fractions respectively and designated as E4-A, E4-B, E4-C, E4-D, E4-E and E6-A, E6-B, E6-C, E6-D respectively.

The fractions as obtained were assayed against *S. oryzae* and *R. dominica* as described in Example 1. The results are presented in Table 8 and Table 9.

TABLE 8

Bioefficacy of E4 and E6 fractions against rice weevil, *Sitophilus oryzae*

| Fraction | 12.5 ppm | | 25 ppm | | 50 ppm | | 100 ppm | |
|---|---|---|---|---|---|---|---|---|
| | % mort. | Avg. No. emerged | % mort. | Avg. No. emerged | % mort. | Avg. No. emerged | % mort. | Avg. No. emerged |
| E4-A | 0.0 | 119 | 1.6 | 139.5 | 0.0 | 100 | 0.0 | 95.24 |
| E4-E | 5.0 | 197 | 5.0 | 132.7 | 8.3 | 145.5 | 8.3 | 137.7 |
| E6-A | 0.0 | 136 | 3.3 | 122.7 | 0.0 | 95.7 | 0.0 | 89.5 |
| E6-C | 0.0 | 162 | 0.0 | 159.7 | 1.6 | 151.7 | 0.0 | 112.5 |
| E6-D | 1.6 | 192 | 1.6 | 193 | 5.0 | 108 | 6.6 | 94.2 |
| Control | 1.6 | 134.7 | 5.0 | 181.5 | 3.3 | 171.7 | 3.3 | 171.7 |

TABLE 9

Bioefficacy of E4 and E6 fractions against lesser grain borer, *Rhozopertha dominica*

| Fraction | 100 ppm | | 50 ppm | | 25 ppm | | 12.5 ppm | |
|---|---|---|---|---|---|---|---|---|
| | % mort. | Avg. No. emerged | % mort. | Avg. No. emerged | % mort. | Avg. No. emerged | % mort. | Avg. No. emerged |
| E4-A | 98.3 | 0.026 | 98.3 | 0.143 | 98.3 | 0.184 | 98.3 | 0.186 |
| E4-B | 98.3 | 0.049 | 91.6 | 0.084 | 91.6 | 0.136 | 88.3 | 0.198 |

TABLE 9-continued

Bioefficacy of E4 and E6 fractions against lesser grain borer, *Rhozopertha dominica*

| Fraction | 100 ppm % mort. | 100 ppm Avg. No. emerged | 50 ppm % mort. | 50 ppm Avg. No. emerged | 25 ppm % mort. | 25 ppm Avg. No. emerged | 12.5 ppm % mort. | 12.5 ppm Avg. No. emerged |
|---|---|---|---|---|---|---|---|---|
| E4-C | 95.0 | 0.049 | 83.3 | 0.14 | 83.3 | 0.107 | 78.3 | 0.274 |
| E4-D | 96.0 | 0.109 | 91.6 | 0.176 | 91.6 | 0.50 | 88.3 | 0.319 |
| E4-E | 96.6 | 0.046 | 88.3 | 0.164 | 88.3 | 0.249 | 81.6 | 0.219 |
| E6-A | 98.3 | 0.029 | 95 | 0.089 | 73.3 | 0.042 | 66.6 | 0.084 |
| E6-B | 91.6 | 0.014 | 91.6 | 0.044 | 90.0 | 0.048 | 90.0 | 0.068 |
| E6-C | 96.6 | 0.042 | 90.0 | 0.037 | 88.3 | 0.054 | 78.3 | 0.044 |
| E6-D | 96.6 | 0.039 | 95.0 | 0.016 | 85.0 | 0.075 | 85.0 | 0.168 |
| Control | 10.00 | 0.107 | 10.00 | 0.107 | 10.00 | 0.107 | 10.00 | 0.107 |

Example 5

Extract S4 as defines above was extracted in petroleum ether and a fat fraction S5 [S4-A] and defatted fraction S6 [S4-B] were obtained. The S6 fraction was partitioned in n-butanol:water to obtain n-butanol soluble S7[S4-B1] and water soluble S8 [S4-B2] fractions.

Extract T1 was extracted in petroleum ether and a fat fraction T1-A and defatted fraction T1-B were obtained. The T1-B fraction was partitioned in n-butanol:water to obtain n-butanol soluble T1-B1 and water soluble T1-B2 fractions.

The three fractions so obtained were assayed at 1000 ppm on wheat against *S. oryzae* and *R. dominica* and presented in Table 10 and Table 11.

TABLE 10

Bioefficacy of Fractions of S4 and T1 tested against rice weevil *Sitophilus oryzae*

| Treatment | % Mortality (at week) | No. F$_1$ Progeny | Progeny/adult day |
|---|---|---|---|
| Control (Acetone) | 00.00 | 96 | 0.33 |
| S5 (S4-A) | 49.00[3] | 29 | 0.12 |
| S6 (S4-B) | 100[2] | 00 | 0.00 |
| Control (Methanol) | 00.00 | 138 | 0.43 |
| S7 (S4-B1) | 100[2] | 01 | 0.02 |
| (T1-B1) | 100[1] | 00 | 0.00 |
| Control (Water) | 00.00 | 185 | 0.57 |
| S8 (S4-B2) | 83.00[3] | 12 | 0.066 |
| (T1-B2) | 46.00[3] | 51 | 0.19 |

[1], [2] and [3]Mortality obtained after 1, 2 and 3 weeks respectively.

TABLE 11

Bioefficacy of fractions of S4 and T1 against lesser grain borer, *Rhizopertha dominica*

| Treatment | % Mortality (at week) | No. F$_1$ Progeny (Avg) | Progeny/adult day |
|---|---|---|---|
| Control (Acetone) | 9.99 | 138 | 0.406 |
| S4-A | 44.31 | 6.5 | 0.03 |
| * S4-B | — | — | — |
| Control (Methanol) | 20 | 137.5 | 0.49 |
| S4-B1 | 92.85 | 02.0 | 0.016 |
| T1-B1 | 100 | 00.0 | 0.00 |
| Control (Water) | 13.33 | 172.5 | 0.585 |
| S4-B2 | 27.07 | 09.0 | 0.034 |
| T1-B2 | 35.53 | 17.75 | 0.073 |

These fractions exhibited 100% mortality and very significantly reduced Progeny/adult day.

Example 6

The active fraction S7 (S4-B1) was formulated into a dust formulation. 50 gm of the active fraction was mixed with 900 gm of precipitated silica. To this mixture, 50 gram of diluent, in this case, china clay, was added. The mixture was thoroughly mixed until all of the active fraction was absorbed into the additives to give a free flowing powder without caking to form lumps to provide 5% Dust Formulation (5D).

TABLE 12

Bioefficacy of dust formulation of active extract on wheat and green gram.

| Treatment (ppm) | % mortality of test insects | | | Progeny/adult day | | |
|---|---|---|---|---|---|---|
| | S. oryzae | R. dominica | C. chinensis | S. oryzae | R. dominica | C. chinensis |
| 0.00 | 0.00 | 03.33 | 29.99 | 0.58 | 0.45 | 01.41 |
| 200 | 100 | 100 | 100 | 00.00 | 00.00 | 00.00 |
| 100 | 100 | 100 | 100 | 00.09 | 00.08 | 00.05 |
| 50 | 100 | 100 | 48.32 | 00.19 | 00.08 | 00.36 |

Conclusion: The dust formulation was toxic to the test insects and reduced the progeny of *S. oryzae* and *R. dominica* by >80% and that of *C. chinensis* by >90%. The insecticidal activity of the fraction so obtained from the stem of *N. foetida* according to the invention is due to the presence of more than one insecticidal component. Thus the chances on insect pests developing resistance are remote as it is exhibiting additive effect due to multiple active components,

TABLE 13

Toxicity of Bio-pesticide formulation 5D

| Criteria | $LD_{50}$ mg/kg | Comment |
|---|---|---|
| Acute oral toxicity study in Swiss albino mouse | >5000 | GHS (Globally Harmonized System) Category: Unclassified |
| Acute oral toxicity study in rat | >5000 | GHS Category: Unclassified |
| Acute dermal toxicity to rat | >2000 | NA |
| Primary skin irritation study in rabbit | — | Non irritant to skin |
| Mucous membrane irritation study in rabbit | | Non irritant to mucous membrane |

Example 7

To study contribution of compounds other than camptothecin (CPT) towards insecticidal active, from active product (145 g, S4B1) camptothecin was removed by column chromatography (CC) and rest of the product was separated into 26 broad fractions (D1-D26) and assayed for their insect control activity. Fraction D4 exhibited toxicity to adults of the rice weevil, *S. oryzae*. Since no other fraction exhibited toxicity to both the test insect species, it appears that the insect toxicity exhibited by the extract S4B1 may be the result of combined effect of activities of the compounds in the extract.

TABLE 14

Bio-efficacy of D4.

| | Sitophilus oryzae | | | Rhizopertha dominica | | |
|---|---|---|---|---|---|---|
| Sample No D4 | % mortality | Av progeny | Progeny/ adult days | % mortality | Av. Progeny | Progeny/ adult days |
| Control | 19.99 | 129.5 | 0.441 | 1.66 | 161 | 0.513 |
| 12.5 ppm | 54.96 | 118.5 | 0.459 | 4.99 | 141 | 0.454 |
| 25 ppm | 78.3 | 106.25 | 0.460 | 23.33 | 80.75 | 0.286 |
| 50 ppm | 59.99 | 105.25 | 0.431 | 3.33 | 97.25 | 0.316 |
| 100 ppm | 26.66 | 104.75 | 0.373 | 1.66 | 77.5 | 0.247 |

Values are averages of four replicates.

Fractions D18, D21, D24 & D25 were very active in reducing the F1 progeny (IGR activity). Adjacent fractions of D17, D22 & D26 exhibited reduced activity indicating reduced titres of the active compounds. However none of these exhibited toxicity to the test insects.

TABLE 15

Fractions exhibiting IGR activity in the test insects.

| | Sitophilus oryzae | | | Rhizopertha dominica | | |
|---|---|---|---|---|---|---|
| Sample No | % mortality | Av progeny | Progeny/ adult days | % mortality | Av. Progeny | Progeny/ adult days |
| D18 | | | | | | |
| Control | 0.0 | 211.5 | 0.663 | 3.33 | 129 | 0.421 |
| 12.5 ppm | 1.66 | 195.5 | 0.577 | 3.33 | 93.25 | 0.275 |
| 25 ppm | 1.66 | 216.5 | 0.632 | 3.33 | 82.75 | 0.244 |
| 50 ppm | 0.0 | 147 | 0.426 | 10 | 20 | 0.064 |
| 100 ppm | 1.66 | 92.25 | 0.344 | 15 | 6.5 | 0.020 |
| D-20 | | | | | | |
| Control | 01.66 | 193.0 | 0.615 | 1.66 | 144.5 | 0.463 |
| 12.5 ppm | 4.99 | 244.25 | 0.788 | 0 | 157.75 | 0.500 |
| 25 ppm | 3.33 | 331.75 | 1.064 | 0 | 116.0 | 0.367 |
| 50 ppm | 3.33 | 292.0 | 0.948 | 1.66 | 81.25 | 0.258 |
| 100 ppm | 1.66 | 306.25 | 0.977 | 0 | 25.5 | 0.079 |
| D-21 | | | | | | |
| Control | 01.66 | 193.0 | 0.615 | 1.66 | 144.5 | 0.463 |
| 12.5 ppm | 3.33 | 254 | 0.814 | 3.33 | 23.5 | 0.0747 |
| 25 ppm | 0.0 | 146.25 | 0.464 | 0 | 19.25 | 0.060 |
| 50 ppm | 6.66 | 118.5 | 0.392 | 1.66 | 8.5 | 0.0265 |
| 100 ppm | 14.99 | 64.25 | 0.230 | 1.66 | 2.25 | 0.0067 |
| D-22 | | | | | | |
| Control | 01.66 | 193.0 | 0.615 | 1.66 | 144.5 | 0.463 |
| 12.5 ppm | 0 | 328 | 1.040 | 0 | 97.5 | 0.309 |
| 25ppm | 8.33 | 226 | 0.746 | 0 | 64 | 0.226 |
| 50 ppm | 0 | 252.25 | 0.800 | 0 | 46.75 | 0.139 |
| 100 ppm | 1.66 | 223.25 | 0.712 | 1.66 | 37.25 | 0.118 |
| D24 | | | | | | |
| Control | 0 | 211.5 | 0.663 | 3.33 | 129 | 0.421 |
| 12.5 ppm | 0 | 151.5 | 0.439 | 10.0 | 21.25 | 0.062 |
| 25 ppm | 1.66 | 141.25 | 0.411 | 20.0 | 16.5 | 0.055 |
| 50 ppm | 0 | 145.5 | 0.421 | 3.33 | 7.0 | 0.020 |
| 100 ppm | 3.33 | 106.75 | 0.320 | 13.33 | 3.75 | 0.011 |
| D-25 | | | | | | |
| Control | 0 | 261.25 | 0.829 | 0.0 | 113.25 | 0.359 |
| 12.5 ppm | 1.66 | 214.25 | 0.683 | 0 | 59.5 | 0.060 |
| 25 ppm | 1.66 | 175.25 | 0.559 | 1.66 | 19.0 | 0.024 |
| 50 ppm | 0 | 125.0 | 0.396 | 1.66 | 7.75 | 0.024 |
| 100 ppm | 1.66 | 56.5 | 0.180 | 3.33 | 5.0 | 0.026 |
| D-26 | | | | | | |
| Control | 0 | 261.25 | 0.829 | 0.0 | 113.25 | 0.359 |
| 12.5 ppm | 0 | 244.5 | 0.776 | 3.33 | 105.75 | 0.341 |
| 25 ppm | 0 | 219.25 | 0.696 | 3.33 | 92.5 | 0.301 |
| 50 ppm | 1.66 | 217.5 | 0.694 | 3.33 | 95.25 | 0.308 |
| 100 ppm | 0 | 208.7 | 0.662 | 0 | 95.25 | 0.188 |

Values are averages of 4 replicates.

From D4 (fraction with insecticidal activity) Pthalate was isolated.

From D18, D21 (fraction exhibiting IGR activity) Pthalate was isolated.

From D24 (fraction exhibiting IGR activity)—Campthothecanoid 1 was isolated.

From D25 (fraction exhibiting IGR activity)—Campthothecanoids 2 and 3 were isolated.

These compounds have not been individually assessed for their insecticidal or IGR activities.

Example 8

Isolation of Phthalate

Fractions D18, D21 and D4 contained phthalate. Fraction D18 and D21 were both subjected separately to CC using successively MeCN:chloroform 2:8 and then gradient of methanol:chloroform from 2 to 10% to collect nine fractions. Fraction D4 was subjected to CC in gradient of MeCN:chloroform from 1 to 20% to collect fourteen fractions. Fractions D18:2, D21:2 and D4:2 contained pure phthalate (1.1 g).

Isolation of Camptothecanoids

Fraction D24:12 (78 mg) was separated by Medium Pressure Liquid Chromatography (MPLC) using gradient of methanol in chloroform from 3 to 25% followed by methanol wash to collect twenty six fractions. Combined fractions 14 to 16 were subjected to preparative TLC in 15% methanol:chloroform and then 20% methanol:chloroform to isolate campptothecanoid 1 (10.2 mg).

Fraction D25:4-5 (180 mg) was separated by MPLC using gradient of methanol in chloroform from 0 to 25% followed by methanol wash to collect twenty two fractions. Fractions 3, 4, 5, 12 and 13 were combined (100 mg) and subjected to CC in gradient of methanol in chloroform from 5 to 25% followed by methanol wash to collect sixteen fractions. Fractions 10-11 and 12-15 contained camptothecanoids 2 and 3. They were separated and purified by preparative TLC in 20% methanol:chloroform to isolate camptothecanoids 2 and 3.

Fraction 14-17 (60 mg) from D25:4-5 contained camptothecanoid 2 which was subjected to CC in gradient of methanol in chloroform from 5 to 25% followed by methanol wash to collect fifteen fractions. From fractions 11-12 camptothecanoid 2, which was isolated by preparative TLC in 15% methanol:chloroform. Fractions 13 and 14-15 contained camptothecanoids 2 and 3. They were separated and purified by preparative TLC in 20% methanol:chloroform to isolate camptothecanoids 2 and 3. Fraction 18-21 from D25:4-5 contained camptothecanoid 3 which was purified by preparative TLC in 20% methanol:chloroform. In total 80 mg and 60 mg of camptothecanoid 2 and 3 were isolated.

Example 9

TABLE 16

Bioassay of Camptothecanoid 1, 2 and 3 and Phthalate:

| Compound* | XTT assay *Mycobacterium tuberculosis* Ra | MTT assay against THP 1 cell line |
|---|---|---|
| | % Inhibition | |
| Camptothecanoid 1 | 48.32 | 70.87 |
| Camptothecanoid 2 | 88.42 | 87.48 |
| Camptothecanoid 3 | 58.96 | 90.20 |
| Phthalate | 45.61 | 20.15 |
| Paclitaxel | — | 61.00 |
| Isoniazid | 0.05** | — |

*inhibition at 100 μg/ml,
**$IC_{90}$ in μg/ml

Example 10

Anti-Mycobacterial Activity

*M. tuberculosis* H37Ra (ATCC 25177) cells, obtained from MTCC (Chandigarh, India), were grown to logarithmic phase (O.D, 0.595~1.0) in a defined medium (*M. pheli* medium) under aerobic conditions in a shaker incubator (Thermo Electron Corporation Model 481) maintained at 150 rpm and 37° C. After growth, the culture was sonicated for 2 min using water bath sonicator. Sonicated cells were used for inoculation in micro plate wells. 250 l of culture containing ~1×10⁵ cells/ml was added to each well of 96 well plates. Camptothecanoid 1, 2 and 3 and Phthalate, 2.5 l, dissolved in DMSO (Sigma), were added to the wells to attain a final concentration of 100 g/ml respectively for screening. Then, the plate was incubated in a $CO_2$ incubator at 37° C. The plate was taken out on the 8th day of incubation to measure the viable cell counts. The optical density of the culture was measured before addition of XTT (Sigma) at 470 nm which was served as a blank for the MIC calculations. XTT, 200 M, was added and incubated for 20 min at 37° C. after shaking for 1 min. After 20 min of incubation, 60 M Menadione (Sigma) was added and incubated at 37° C. for 40 min after mixing of 1 min. Finally, the optical density of the suspension was measured at 470 nm by using microplate reader. Isoniazid (Sigma) was used as a positive control.

Example 11

Anti Proliferative Activity-MTT Cell Proliferation Assay on Human Thp-1 Cell Line Camptothecanoid 1, 2 and 3 and Phthalate were tested for their inhibitory effect on THP-1 cells. About 10,000 cells were taken per well in 96-well tissue culture plates and treated with test samples at 100 μg/ml for 72 h. Vehicle control (DMSO, 1%) and positive control (Paclitaxel, 100 μg/ml) was run simultaneously. Cell proliferation was assessed with 10 μl from 5 mg/ml stock solution of tetrazolium salt (MTT) dissolved in cell culture medium and subsequently incubated for additional 1 h at 37° C., 5% of $CO_2$ and 95% humidity in incubator. The violet coloured formazan crystals formed were solubilized in 200 μl of isopropanol and incubated for another 4 h. The optical density was read on a micro plate reader (Spectramax plus384 plate reader, Molecular Devices Inc) at 490 nm filter against a blank prepared from cell-free wells. Absorbance given by cells treated with the carrier DMSO alone was taken as 100% cell growth (Table 2).

Example 12. Activity Data of Fractions Containing Compounds of General Formula 1 and Formula 2

Fractions NCL49-D24 and NCL49-D25 containing camptothecanoids 2 and 3 displayed potent insect regulatory activity against *Rhizopertha dominica* and good activity against *Sitophilus oryzae*.

Similarly fraction NCL49-D21 containing phthalate displayed potent insect regulatory activity against *Rhizopertha dominica* and good activity against *Sitophilus oryzae*.

TABLE 17

| | *Sitophilus oryzae* | | | *Rhizopertha dominica* | | |
|---|---|---|---|---|---|---|
| Sample Code No | % mortality | Av progeny | Progeny/adult days | % mortality | Av. Progeny | Progeny/adult days |
| Pthalate (D-21) | | | | | | |
| Control | 01.66 | 193.0 | 0.615 | 1.66 | 144.5 | 0.463 |
| 12.5 ppm | 3.33 | 254 | 0.814 | 3.33 | 23.5 | 0.0747 |
| 25 ppm | 0.0 | 146.25 | 0.464 | 0 | 19.25 | 0.060 |
| 50 ppm | 6.66 | 118.5 | 0.392 | 1.66 | 8.5 | 0.0265 |
| 100 ppm | 14.99 | 64.25 | 0.230 | 1.66 | 2.25 | 0.0067 |
| Camptothecanoids - 1 (D24) | | | | | | |
| Control | 0 | 211.5 | 0.663 | 3.33 | 129 | 0.421 |
| 12.5 ppm | 0 | 151.5 | 0.439 | 10.0 | 21.25 | 0.062 |

TABLE 17-continued

| Sample Code No | Sitophilus oryzae | | | Rhizopertha dominica | | |
|---|---|---|---|---|---|---|
| | % mortality | Av progeny | Progeny/ adult days | % mortality | Av. Progeny | Progeny/ adult days |
| 25 ppm | 1.66 | 141.25 | 0.411 | 20.0 | 16.5 | 0.055 |
| 50 ppm | 0 | 145.5 | 0.421 | 3.33 | 7.0 | 0.020 |
| 100 ppm | 3.33 | 106.75 | 0.320 | 13.33 | 3.75 | 0.011 |
| Camptothecanoid - 2 & 3 (D-25) | | | | | | |
| Control | 0 | 261.25 | 0.829 | 0.0 | 113.25 | 0.359 |
| 12.5 ppm | 1.66 | 214.25 | 0.683 | 0 | 59.5 | 0.060 |
| 25 ppm | 1.66 | 175.25 | 0.559 | 1.66 | 19.0 | 0.024 |
| 50 ppm | 0 | 125.0 | 0.396 | 1.66 | 7.75 | 0.024 |
| 100 ppm | 1.66 | 56.5 | 0.180 | 3.33 | 5.0 | 0.026 |

Values are averages of 4 replicates.

Advantages of the Invention

The insecticidal enriched extract (biopesticide) prepared from the stem of *Nothapodites foetida* (Wight) Sleumer (formerly *Mappia foetida* (Miers) is
- useful for the insect free storage and transport of grains and seed.
- non-toxic to non-target organisms.
- biodegradable and hence has good safety profile.
- has multiple active ingredients and hence has less prone for the development of resistance.
- acts with multiple mechanisms (insecticidal, growth inhibition) and hence less prone for the development of resistance.
- insecticidal activity is ascribed to compound/s other than camptothecin an anticancer drug.

The invention claimed is:

1. A method of protecting grain or seed from insect infestation, the method comprising:
   treating a grain or seed with an insecticidal composition comprising:
   a compound of general formula:

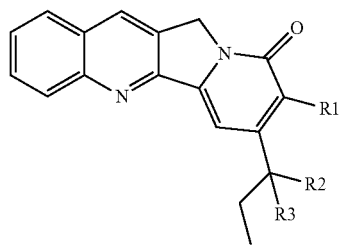

General formula 1 wherein
   R1 is CH$_3$ or CH$_2$OAc,
   R2 is COOH or

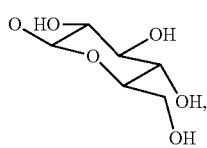 [SMILES: OCC1OC(O)C(O)C(O)C1O]

and
   R3 is H or OH; and
   a compound of formula 2:

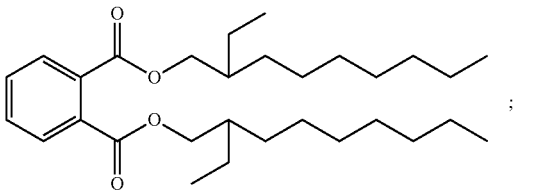

Formula 2 and
   a pharmaceutically acceptable additive useful for the protection of stored grains and seed from insect infestation,
   wherein the method is effective for protecting grain or seed from insect infestation.

2. The method as claimed in claim 1, wherein the compound of general formula 1 is:

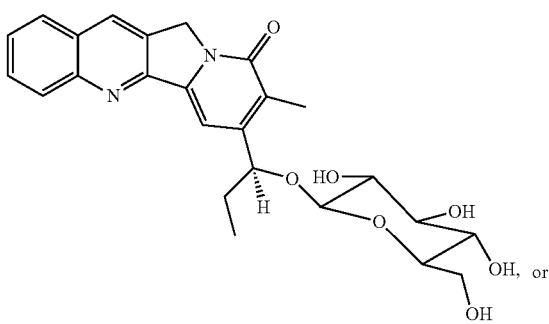

Camptothecanoid-1 (D3)

or

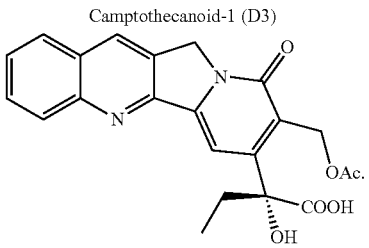

Camptothecanoid-2 (CPT D5)

3. The method as claimed in claim 1, wherein the composition is non-toxic to non-target insect pests.

4. The method as claimed in claim 1, wherein the composition is active against stored product insect pests.

5. The method as claimed in claim 1, wherein the additive is selected from the group consisting of diluents, solvents, surfactants and carriers.

6. The method as claimed in claim 1, wherein the composition is in the form of spray, dust, powder, tablet or pellets.

7. The method as claimed in claim 1, wherein the composition is effective for more than 100 days with a reduction in F1 progeny of infestants.

8. The method as claimed in claim 1, wherein the composition exhibits 100% mortality of rice weevil *Sitophilus oryzae*, lesser grain borer *R. dominica* and *Callosobruchus chinensis*.

9. A process for the preparation of compounds of general formula 1 and formula 2 as claimed in claim 1, from the stem of *N. foetida* comprising the steps of:

i. drying the stem of the *Nothapodites foetida* in shade followed by cutting into small pieces and pulverizing;

ii. extracting the powder of step [i] with methanol and designating the extract as S1;

iii. extracting the residue of step [ii] with methanol and designating the extract as S2;

iv. extracting the residue of step [iii] with methanol and designating the extract as S3;

v. stripping off methanol from extracts 1, 2 and 3 as obtained in steps (ii), (iii) and (iv) respectively, pooling and defatting the residue in petroleum ether;

vi. optionally, combining the extracts 1, 2 and 3 as obtained in steps (ii), (iii) and (iv) respectively to yield an extract designated as S4;

vii. stripping off methanol from extract 4 as obtained in step (vi) followed by defatting thereof in petroleum ether to obtain extract S5 and defatted residue S6;

viii. partitioning the defatted residues S6 as obtained in step [v] and/or [vii] in n-butanol designated as S7 and in water designated as S8;

ix. stripping off the solvent to obtain the insecticidal enriched bioactive extract;

x. removing camptothecin by column chromatography (CC) to obtain fraction D1-D26;

xi. subjecting fraction D1-D26 to CC using successively methyl cynate and chloroform (2:8) and then a gradient of methanol and chloroform to obtain fractions D24, D25, D18, D21 and D4;

xii. subjecting fraction D18, D21 and D4 to CC as obtained in step (xi) in a gradient of MeCN:chloroform to obtain fractions D18:2, D21:2 and D4:2 containing pure phthalate of general formula 2;

xiii. separating fraction D24 as obtained in step (xi) using a gradient of methanol in chloroform followed by a methanol wash to obtain fraction D24:12 containing compound campptothecanoid 1 of general formula 1;

xiv. separating fraction D25 as obtained in step (xi) using a gradient of methanol in chloroform to obtain fraction D25:4-5 containing compounds camptothecanoids 2 and 3 of general formula 1.

10. A method of protecting grain or seed from insect infestation, the method comprising:
treating a grain or seed with an insecticidal composition comprising:
a compound of the formula:

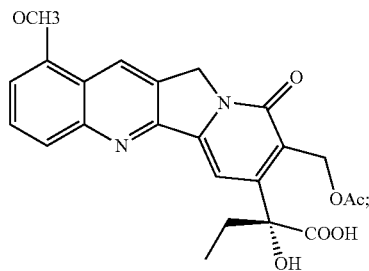

Camptothecanoid-3 (CPT D6)

and
a compound of formula 2:

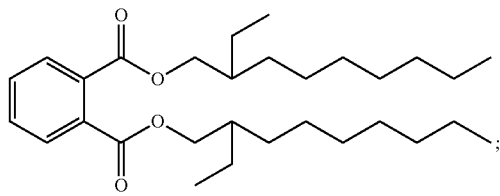

Formula 2 and
a pharmaceutically acceptable additive useful for the protection of stored grains and seed from insect infestation,
wherein the method is effective for protecting grain or seed from insect infestation.

11. The method of claim 3, wherein the non-target insect pest is selected from the group consisting of aphids, *thrips*, diamondback moth, tobacco caterpillar, gram pod borer, bihar hairy caterpillar, potato tuber moth, tea mosquito, red spider mite, and Mexican beetle.

12. The method of claim 4, wherein the stored product insect pest is selected from the group consisting of red flour beetle, *Tribolium castaneum*, lesser grain borer, *Rhizopertha dominica*, pulse beetle, *Callosobruchus chinensis*, almond moth, *Ephestia cautella*, rice moth, and *Corcyra cephalonica*.

* * * * *